(12) United States Patent
Yuan et al.

(10) Patent No.: US 6,552,071 B2
(45) Date of Patent: Apr. 22, 2003

(54) METHODS FOR TREATING CELL DEATH DISEASES AND INFLAMMATION

(75) Inventors: Junying Yuan, Newton, MA (US); Masuko Kobori, Ibaraki (JP); Zhen Yang, Brookline, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 0 days.

(21) Appl. No.: 09/735,848

(22) Filed: Dec. 13, 2000

(65) Prior Publication Data

US 2002/0049251 A1 Apr. 25, 2002

Related U.S. Application Data

(60) Provisional application No. 60/170,310, filed on Dec. 13, 1999.

(51) Int. Cl.[7] .................... A61K 31/366; C07D 311/08; C07D 307/83
(52) U.S. Cl. ....................... 514/453; 549/276; 549/469; 549/471
(58) Field of Search ............................... 549/276, 469, 549/471; 514/453

(56) References Cited

U.S. PATENT DOCUMENTS

| 5,130,133 A | 7/1992 | Rajagopalan et al. ..... 424/195.1 |
| 5,559,146 A | 9/1996 | Sablon ........................ 514/468 |

FOREIGN PATENT DOCUMENTS

| JP | 2000-344630 | 12/2000 |

OTHER PUBLICATIONS

Kamalam et al., "Estimation of Bioactive Principle, Wedelolactone in Wedelia Chinensis (Osbeck), Merr. In *In Vitro*," *Indian Drugs* 36:484–486 (1999).

Maeda et al., "Studies on the preparation of bioactive lignans by oxidative coupling reaction. III. Synthesis of polyphenolic benzofuran and coumestan derivatives by oxidative coupling reaction of methyl (E)–3–(4–Hydroxy–2–methoxyphenyl)propenoate and their inhibitory effect on lipid peroxidation," *Chem. Pharm. Bull.* 42:2536–2545 (1994).

Melo et al., "Ability of wedelolactone, heparin, and para–bromophenacyl bromide to antagonize the myotoxic effects of two crotaline venoms and their $PLA_2$ myotoxins," *Toxicon* 37:199–215 (1999).

Melo et al., "Inhibition of the myotoxic and hemorrhagic activities of crotalid venoms by *Eclipta prostrata* (asteraceae) extracts and constituents," *Toxicon* 32:595–603 (1994).

Mors et al., "Neutralization of lethal and myotoxic activities of South American rattlesnake venom by extracts and constituents of the plant *Eclipta prostrata* (asteraceae)," *Toxicon* 27:1003–1009 (1989).

Nan et al., "A new complex of palladium–thiourea and carbon tetrabromide catalyzed carbonylative annulation of o–hydroxylarylacetylenes: Efficient new synthetic technology for the synthesis of 2,3–disubstituted benzo[]furans," *Organic Letters* 2:297–299 (2000).

Pandey et al., "Mushroom tyrosinase catalyzed synthesis of the coumestans, benzofuran derivatives and related heterocyclic compounds," *Tetrahedron* 45:6867–6874 (1989).

Wagner et al., "In vitro 5–lipoxygenase inhibition by *Eclipta alba* extracts and the coumestan derivative wedelolactone," *Planta Medica* 5:374–377 (1986).

Wagner et al., "Coumestans as the main active principles of the liver drugs *Eclipta alba* and *Wedelia calendulacea*," *Planta Medica* 5:370–374 (1986).

Wong et al., "Wedelolactone and coumestan derivatives as new antihepatotoxic and antiphlogistic principles," *Arzneim.–Forsch/Drug Res.* 38:661–665 (1988).

*Primary Examiner*—Ba K. Trinh
(74) *Attorney, Agent, or Firm*—Clark & Elbing LLP; Kristina Bieker-Brady

(57) ABSTRACT

The present invention features methods and compounds for treating or preventing a cell death disease or inflammation, and methods for synthesizing wedelolactone.

16 Claims, 28 Drawing Sheets

29. All carbon silyl linker 28. amide based silyl linker

METHODS FOR TREATING CELL DEATH DISEASES AND INFLAMMATION

CROSS REFERENCE TO RELATED APPLICATIONS

This application claims priority from U.S. Provisional Application Ser. No. 60/170,310, filed Dec. 13, 1999.

BACKGROUND OF THE INVENTION

In general, the invention features methods and compounds for treating or preventing a cell death disease or inflammation.

A feature of many diseases, for example, neurodegenerative diseases, is the occurrence of cell death. While the death of any type of cell in the body as a result of a disease is a medical concern, the effects of the death of certain types of cells, for example neuronal cells, are particularly disturbing, as these cell types do not readily regenerate. Therefore, understanding the mechanisms that regulate cell death is essential to being able to prevent or treat conditions, such as neurodegenerative diseases.

Research has shown that caspases play a central role in the induction of apoptosis. For example, caspase-11 has been shown to modulate both cytokine production and apoptosis, and to be induced upon ischemic brain injury (Wang et al., J. Biol. Chem. 271:20580–20587, 1996; Wang et al., Cell 92:501–509, 1998). These studies suggest that caspase-11 is involved in mediating cell death and inflammatory responses. Discovery of a compound that modulates the expression of caspases and/or the occurrence of inflammation or cell death would provide a useful therapeutic for treating conditions involving inflammation or conditions in which cell death occurs, and also for preventing such conditions.

SUMMARY OF THE INVENTION

The present invention features methods and compounds for treating or preventing inflammation or a cell death disease. The methods involve the use of the plant extract wedelolactone and may be particularly useful for treating neurodegenerative diseases.

Accordingly, in a first aspect, the invention features a method for treating or preventing a cell death disease in a subject, comprising administering wedelolactone, or a derivative or salt thereof, to the subject. The cell death disease of the first aspect of the invention is not caused by hepatotoxicity.

In a second aspect, the invention features a method for treating or preventing inflammation in a subject, comprising administering wedelolactone, or a derivative or salt thereof, to the subject.

In one embodiment of the above aspects of the invention, the wedelolactone is present in an extract from a plant. Preferably the wedelolactone is substantially pure.

In a third aspect, the invention features a method for treating or preventing a cell death disease in a subject, involving administering to the subject a chemical compound in a pharmaceutically acceptable carrier, having the formula:

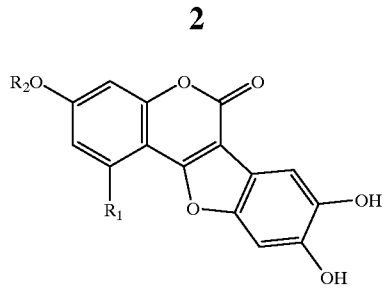

where $R_1$ is selected from the group consisting of H, OH, and $OCH_3$; and $R_2$ is selected from the group consisting of H, $CH_3$, and $(CH_2)_x CH_3$, where x is a positive integer. This method is not used to treat a cell death disease caused by hepatotoxicity.

In a fourth aspect, the invention features a method for treating or preventing inflammation in a subject, involving administering to the subject a chemical compound in a pharmaceutically acceptable carrier, having the formula:

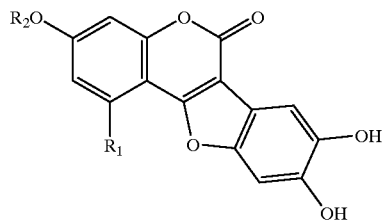

where $R_1$ is selected from the group consisting of H, OH, and $OCH_3$; and $R_2$ is selected from the group consisting of H, $CH_3$, and $(CH_2)_x CH_3$, where x is a positive integer.

In a preferred embodiment of the third or fourth aspects of the invention, in the compound, $R_1$ is OH and $R_2$ is $CH_3$.

In one embodiment of the first or third aspect of the invention, the cell death disease is a neurodegenerative disease, for example, ischemic brain injury or stroke. In another embodiment of any of the above aspects of the invention, the subject is a mammal, such as a human or a mouse.

In a fifth aspect, the invention features a chemical compound in a pharmaceutically acceptable carrier, having the formula:

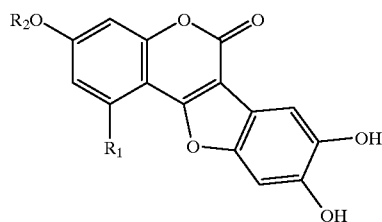

where $R_1$ is selected from the group consisting of H, OH, and $OCH_3$; and $R_2$ is selected from the group consisting of H, $CH_3$, and $(CH_2)_x CH_3$, where x is a positive integer.

In a preferred embodiment of the fifth aspect of the invention, in the compound, $R_1$ is OH and $R_2$ is $CH_3$.

In a sixth aspect, the invention features a method of synthesizing a 2,3-disubstituted benzo[b]furan, involving subjecting a molecule having the formula:

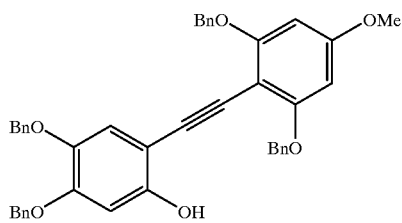

to carbonylative heteroannulation.

In one embodiment of the sixth aspect of the invention, the molecule is in reaction with CO and $CH_3OH$. In another embodiment, the carbonylative heteroannulation occurs in the presence of $PdI_2$-thiourea, $CBr_4$, and $CsCO_3$.

In a seventh aspect, the invention features a method of synthesizing wedelolactone, involving subjecting a molecule having the formula:

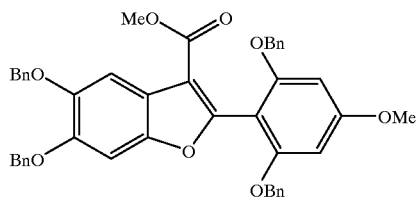

to lactonization.

By "treating" is meant to submit or subject an animal, cell, lysate or extract derived from a cell, or a molecule derived from a cell to a compound that decreases cell death or inflammation.

By a "cell death disease" is meant a disease that results in the death of a cell or a population of cells. As used herein, the cell death disease is not caused by hepatotoxicity. The occurrence of cell death can be measured by determining cellular ATP levels, wherein a cell that is undergoing cell death has a decreased level of cellular ATP compared to a control cell. The occurrence of cell death may also be measured by staining with a vital dye, for example, trypan blue, where a cell that is dead will be stained with the vital dye, and a cell that is not dead will not be stained with the dye. The occurrence of cell death can also be measured by contacting a cell with Hoescht stain and viewing it for morphological indications of cell death. Such indications include nuclear fragmentation.

By a "neurodegenerative disease" is meant a disease characterized by neuronal cell death. Examples of neurodegenerative diseases include, but are not limited to, Alzheimer's disease, Huntington's disease and related polyglutamine expansion diseases, ischemic brain injury, stroke, amyotropic lateral sclerosis, multiple sclerosis, Lewy body disease, Menkes disease, Wilson disease, Creutzfeldt-Jakob disease, and Fahr disease.

By a "neuron" is meant a cell of ectodermal embryonic origin derived from any part of the nervous system of an animal. Neurons express well-characterized neuron-specific markers, including neurofilament proteins, MAP2, and class III tubulin. Included as neurons are, for example, hippocampal, cortical, midbrain dopaminergic, motor, sensory, sympathetic, septal cholinergic, and cerebellar neurons.

By a "derivative" is meant a structural derivative having a chemical modification of the compound that does not modify the ultimate level of cell death or inflammation, but that does enhance bioavailability, solubility, or stability in vivo or ex vivo or that reduces the toxicity or dosage required. Such modifications are known to those skilled in the field of medicinal chemistry. As used herein, a derivative of wedelolactone may be synthesized from the purified wedelolactone extract, or may be chemically synthesized using reagents other than the purified wedelolactone extract.

By "substantially pure" is meant a compound that is at least 60%, by weight, free from proteins and naturally-occurring organic molecules with which it is naturally associated. Preferably the preparation is at least 75%, more preferably 90%, and most preferably at least 99%, by weight, chemical compound, e.g., wedelolactone. A purified compound may be obtained, for example, by high pressure liquid chromatograph, thin layer chromatography, or by synthesizing it.

By "preventing a cell death disease" is meant decreasing the number of cells that undergo cell death relative to an untreated control. As used herein, cell death may be inhibited. Preferably cell death is decreased 10% relative to a control compound with no activity in preventing cell death. More preferably cell death is decreased 50% relative to a control. Most preferably cell death is decreased 90% relative to a control.

By a "plant extract" is meant a compound or mixture of compounds that are obtained from a plant. A plant extract may be obtained from a plant, for example, by chopping up the plant into small pieces, treating the plant with high pressure, distilling the plant, or treating the plant with solvents.

By "treating" is meant submitting or subjecting an animal to a compound that promotes the elimination or reduction of a disease or condition or symptoms of a disease or condition, or that slows the progression of the disease. For example, an animal may be treated with plant extracts, synthesized organic molecules, naturally-occurring organic molecules, peptides, polypeptides, nucleic acid molecules, or components thereof.

By a "candidate modulatory compound" is meant a chemical, be it naturally-occurring or artificially-derived, that is surveyed for its ability to modulate caspase-11 biological activity, or the occurrence of cell death or inflammation by employing one of the assay methods described herein. Compounds may include, for example, naturally-occurring organic molecules, synthesized organic molecules, polypeptides, nucleic acid molecules, or components thereof.

By "caspase-11 biological activity" is meant any activity of caspase-11 found in cells. This includes the level of caspase-11 nucleic acids or polypeptides, and the effect of caspase-11 on substrates. This also includes the effect of caspase-11 on cell proliferation and cell death.

The present invention provides a number of advantages. For example, the methods described herein allow for the treatment or prevention of a cell death disease or inflammation. Substantially pure wedelolactone or a derivative or salt thereof, may be used to treat such conditions. A plant extract containing wedelolactone may also be used to treat or prevent inflammation or a cell death disease.

Other features and advantages of the invention will be apparent from the following detailed description and from the claims.

BRIEF DESCRIPTION OF THE DRAWINGS

FIG. 17 is a schematic representation of the steps involved in the synthesis of substituted methyl benzo[b]furan-3-carboxalate molecule 17a.

DETAILED DESCRIPTION OF THE INVENTION

Figure 1:
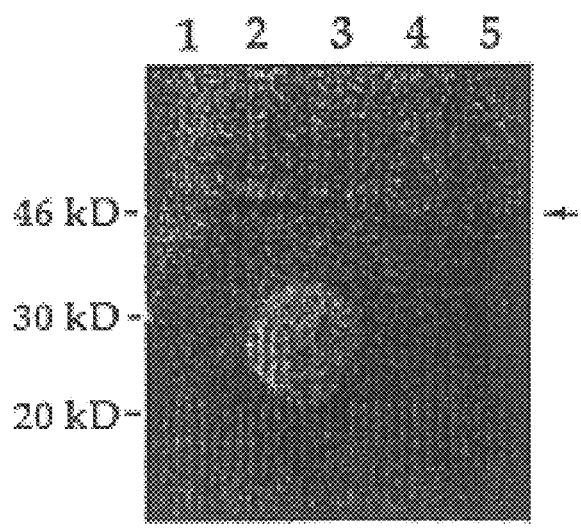
FIG. 1 is a scanned image of a Western blot analysis of the inhibition of caspase-11 induction by *Eclipta prostrata* L. Mice were injected intraperitoneally with lipopolysaccharide (LPS; 40 μg/g body weight) either with or without Eclipta prostrata L. extract. Four hours after injection, the mice were sacrificed and their spleens were removed and prepared for western blot. The western blot was probed with anti-caspase-11 monoclonal antibody. Lane 1, caspase-11 mutant mouse injected with LPS; lane 2, a wild type mouse injected with LPS; lane 3, a wild type mouse injected with LPS plus 40 mg of Eclipta prostrata L. extract; lane 4, a wild type mouse injected with LPS plus 25 mg of Eclipta prostrata L. extract; lane 5, a wild type mouse injected with LPS plus 50 mg of Eclipta prostrata L. extract.

The Role of Caspase-11 in Modulating Cell Death and Inflammation

Previous studies have indicated that caspase-11 plays a role in mediating both cell death and inflammatory responses (Wang et al., J. Biol. Chem. 271:20580–20587, 1996; Wang et al., Cell 92:501–509, 1998). For example, overexpression of caspase-11 in Rat-1 and HeLa cells induces apoptosis. In contrast, caspase-11 knockout mice are resistant to ischemic brain injury-induced apoptosis. In addition, caspase-11 mutant embryonic fibroblast cells are resistant to apoptosis induced by overexpression of the cell death promoting gene ICE. These results demonstrate that caspase-11 is involved in mediating cell death.

These same studies revealed that caspase-11 is involved in mediating inflammatory responses. For example, caspase-11 promotes pro-interleukin 1 beta processing by ICE, and its expression is induced upon stimulation with LPS. In addition, caspase-11 knockout mice are resistant to the LPS model of septic shock, indicating that this gene is involved in mediating inflammatory responses.

Induction of Caspase-11 is Mediated Through the NF-κB Pathway

NF-κB is a dimeric transcription factor consisting of two subunits, Rel A (p65) and NF-κB 1 p50. NF-κB exists in the cytoplasm in an inactive form by virtue of its association with an inhibitor IκBα. Upon stimulation by appropriate signals, IκBα is selectively phosphorylated by the IκB kinase complex and is subjected to degradation through a ubiquitin/proteasome pathway. Upon degradation of IκBα, NF-κB undergoes rapid nuclear translocation and induces gene expression. A myriad of pathological stimuli have been shown to induce NF-κB activity. This list includes bacterial endotoxins, proinflammatory cytokines, viral infections, parasites, UV irradiation, chemotherapeutic agents, oxidative stress and DNA damage. Aberrant regulation of NF-κB has been associated with pathogenesis of several diseases, including cancer. The pharmaceutical industry has made considerable efforts to identify novel inhibitors of NF-κB activation.

Expression of caspase-11 is also induced by TNF-α and IL-1β (Y. Jung and J. Yuan, unpublished data). TNF-α and IL-1β are known to induce multiple biological responses through NF-κB. Recently, it has been shown that NF-κB is activated and plays a key role in mediating cell death in mouse focal cerebral ischemia (Schneider et al., Nat. Med. 5:554–559, 1999). These observations have led to the examination of the possible involvement of NF-κB in caspase-11 induction. NF-κB (+/+) wild type, p65 (−/−) mutant (Beg et al., Nature 376:167–170, 1995), and p65 (−/−)/p50 (−/−) double mutant 3T3 cells (Sha et al., Cell 80:321–330, 1995) were examined for the regulation of caspase-11 induction. Treatment of wild type 3T3 cells with TNF-α, IL-1β, or LPS induced caspase-11 expression. A mutation in NF-κB p65 blocked the ability of TNF-α but not that of IL-1β and LPS, to induce caspase-11 expression; whereas inactivation of both NF-κB p65 and p50 subunits are needed to inhibit the caspase-11 expression induced by IL-1β and LPS. These results suggest that NF-κB is essential for the induction of caspase-11 by cytokines; furthermore, the effect of TNF-α may be mediated through p65 only, whereas signals of LPS and IL-1β may be mediated through either p65 or p50.

Identification of Modulators of Caspase-11 Expression, Cell Death, and Inflammatory Responses Given the role that caspase-11 plays in modulating cell death and inflammatory responses, it is believed that compounds that modulate the expression or activity of caspase-11 would also be useful in treating or preventing a cell death disease or inflammation.

To identify modulators of caspase-11 expression or activity, a tissue culture model of caspase-11 induction was generated. In this model, BalbC/3T3 cells normally express undetectable levels of caspase-11 biological activity, as measured by Western blot analysis. However, upon contacting the cells with LPS for 6 hours, caspase-11 biological activity was clearly induced. A caspase-11 modulatory compound may be administered to the cells prior to administration of LPS, and then caspase-11 biological activity may be measured at a specific time after addition of LPS to the culture media of the cells. A caspase-11 modulatory compound that suppresses the LPS-induced biological activity of caspase-11 is considered to be a compound that modulates not only caspase-11 expression, but also cell death or inflammation.

Alternatively, the biological activity of caspase-11 may be measured using other standard techniques. For example, caspase-11 levels may be measured by immunoprecipitation techniques. In addition, the measurement of biological activity may include the measurement of caspase-11 nucleic acid levels, the effect of caspase-11 on a target molecule, or the effect of caspase-11 on cell proliferation or cell death. For example, standard Northern blot analysis (Ausubel et al., supra) using a caspase-11 cDNA (or cDNA fragment) as a hybridization probe can be used to measure levels of caspase-11 expression. The level of caspase-11 RNA expression in the presence of the candidate molecule is compared to the level measured for the same cells in the same culture medium but in the absence of the candidate molecule.

Caspase-11 modulatory compounds may be purified (or substantially purified) molecules or may be one component of a mixture of compounds (e.g., an extract or supernatant obtained from cells; Ausubel et al., *Current Protocols in Molecular Biology*, John Wiley & Sons, New York, N.Y., 1994). In a mixed compound assay, caspase-11 expression is tested against progressively smaller subsets of the candidate compound pool (e.g., produced by standard purification techniques, such as HPLC or FPLC) until a single compound or minimal compound mixture is demonstrated to modulate caspase-11 expression.

Alternatively, or in addition, candidate caspase-11 modulatory compounds may be screened for those that modulate caspase-11 -mediated inhibition of cell proliferation. In this approach, the degree of cell proliferation in the presence of a candidate compound is compared to the degree of cell proliferation in its absence, under equivalent conditions. Again, such a screen may begin with a pool of candidate compounds, from which one or more useful modulatory compounds are isolated in a step-wise fashion. Cell proliferation activity may be measured by any standard assay, such as the mixed tumor transplantation (MTT) assay.

The identification of modulators of caspase-11, cell death, or inflammation can also be achieved by measuring the level of cell death that occurs in a population of cells contacted with a candidate compound. Cell death can be measured by determining cellular ATP levels, wherein a cell that is undergoing cell death has a decreased level of cellular ATP compared to a control cell that is not exposed to the test compound. Cell death may also be measured by staining with a vital dye, for example, trypan blue, wherein a dead cell will be stained with the vital dye, and a living cell will not be stained with the dye. Cell death may also be measured using any technique known to those skilled in the fields of molecular and cell biology.

Since caspase-11 induction is mediated through the activation of the NF-κB pathway, as discussed above, an alternative for the identification of modulators of caspase-11, cell death, or inflammation approach is to directly screen for inhibitors of the NF-κB pathway. This can be done, for example according to the following method, based on the T-Rex tetracycline inducible system (Invitrogen). To generate an NF-κB responsive system, the NF-κB response element is introduced into pcDNA6/TR vector upstream from the tetracycline repressor gene (TetR) (Invitrogen) replacing the constitutively active CMV promoter. In this new pNFkB-TR vector, expression of TetR protein is controlled by NF-κB induction. Luciferase activity is selected as an optimal output for the screen due to its high sensitivity and low background. Therefore, the Luc gene from the pGL3 vector (Promega) is introduced into the tetracycline operator-containing pTO vector (Invitrogen). Overall, in this system induction of NF-κB activity in response to LPS results in a reduction in luciferase expression. Activation of NF-κB results in an induction of TetR expression, which binds to the tetracycline operator in pTO-Luc vector and inhibits luciferase expression. Attenuation of NF-κB induction by a small molecule inhibitor results in an increase in luciferase expression providing a positive readout, rather than a negative readout. This allows for the distinction between selective NF-κB repressors and generally toxic compounds that occur in a system with a negative readout.

A compound that is identified as being a modulator of caspase-11, cell death, or inflammation can be tested in animal models. For example, a candidate compound can be injected intraperitonally into animals (e.g., mice) with a lethal dose of LPS (for example, 40 mg/kg). The animals are then monitored for symptoms of septic shock, including shivering, fever, lethargy, watery eyes and ultimately death. A candidate compound that results in mice exhibiting less severe septic shock symptoms, compared to control mice (receiving LPS, but no candidate compound) is a compound that can be used to treat cell death diseases and inflammation.

Structural Derivatives of Compounds That Modulate Caspase-11 Expression or Activity, Cell Death, or Inflammation The synthesis of wedelolactone has been the subject of many investigations (Pandey et al., Tetrahedron 45:6867–6874, 1989). Our approach to the synthesis of wedelolactone employs a similar conventional route disclosed by Pandey et al. (supra) that features tyrosinase oxidation of catechol to synthesize the o-quinone from catechol. The o-quinone can react with different substituted 4-hydroxyl-coumarins to give the wedelolactone related molecules. These methods are described in detail in Example 5. Alternatively, wedelolactone may be synthesized according to the methods described in detail in Example 6.

In addition, the use of both solution-phase synthesis and combinatorial synthesis of structural derivatives of wedelolactone may be used and integrated in the search for ideal mimics of wedelolactone that are more efficacious. The probability of finding interesting mimics of wedelolactone with improved pharmacological profiles from a large number of structural derivatives is quite high and the testing for efficacy is readily performed, as described herein.

Therapy

A compound identified as able to modulate caspase-11 biological activity or to decrease cell death, wherein the cell death is not caused by hepatotoxicity, or to decrease inflammation using any of the methods described herein may be administered to patients or animals with a pharmaceutically-acceptable diluent, carrier, or excipient, in unit dosage form. The chemical compounds for use in such therapies may be produced and isolated by any standard technique known to those in the field of medicinal chemistry. Conventional pharmaceutical practice may be employed to provide suitable formulations or compositions to administer the identified compound to patients suffering from a cell death disease or inflammation. Administration may begin before the patient is symptomatic.

Any appropriate route of administration may be employed. For example, the therapy may be administered either directly to the site of a predicted cell death or inflammation event (for example, by injection) or systemically (for example, by any conventional administration technique). Administration of the compound may also be parenteral, intravenous, intraarterial, subcutaneous, intramuscular, intracranial, intraorbital, ophthalmalic, intraventricular, intracapsular, intraspinal, intracisternal, intraperitoneal, intranasal, aerosol, by suppositories, or oral administration. Therapeutic formulations may be in the form of liquid solutions or suspensions; for oral administration, formulations may be in the form of tablets or capsules; and for intranasal formulations, in the form of powders, nasal drops, or aerosols. The dosage of the therapeutic compounds in a pharmaceutically acceptable formulation depends on a number of factors, including the size and health of the individual patient. The dosage to be delivered may be determined by one skilled in the art.

Methods well known in the art for making formulations are found, for example, in "Remington: The Science and Practice of Pharmacy" ((19th ed.) ed. A. R. Gennaro AR., 1995, Mack Publishing Company, Easton, Pa.). Formulations for parenteral administration may, for example, contain excipients, sterile water, or saline, polyalkylene glycols such as polyethylene glycol, oils of vegetable origin, or hydrogenated napthalenes. Biocompatible, biodegradable lactide polymer, lactide/glycolide copolymer, or polyoxyethylene-polyoxypropylene copolymers may be used to control the release of the compounds. Other potentially useful parenteral delivery systems for compounds that decreases necrosis include ethylene-vinyl acetate copolymer particles, osmotic pumps, implantable infusion systems, and liposomes. Formulations for inhalation may contain excipients, for example, lactose, or may be aqueous solutions containing, for example, polyoxyethylene-9-lauryl ether, glycocholate and deoxycholate, or may be oily solutions for administration in the form of nasal drops, or as a gel.

If desired, treatment with a compound identified according to the methods described above, may be combined with more traditional therapies for a disease characterized by cell death, for example, tacrine hydrochloride for the treatment of Alzheimer's disease, or interferon β-1a for the treatment of multiple sclerosis. Similarly, treatment with a compound identified according to the methods described above, may be combined with more traditional therapies for inflammation, for example, nonsteroidal anti-inflammatory drugs or indomethicin.

Preventative Anti-cell Death Therapy

In a patient diagnosed with a cell death disease (e.g., a neurodegenerative disease, such as Alzheimer's disease, stroke, or Huntington's disease), any of the above therapies may be administered before the occurrence of the disease phenotype. In particular, compounds shown to decrease cell death may be administered by any standard dosage and route of administration (as described above).

The methods of the instant invention may be used to prevent or treat a cell death disease or inflammation, as described herein, in any mammal, for example, humans, domestic pets, or livestock.

The following examples are provided to illustrate the invention. These examples should not be construed as limiting.

EXAMPLE 1

Inhibition of Caspase-11 Induction and LPS-induced Lethality by *Eclipta prostrata* L. Extracts Dried *Eclipta prostrata* L. was extracted by boiling it in water. *Eclipta prostrata* L. (EP) extract was then co-injected intraperitonally with a lethal dose of LPS (40 mg/kg) into 10 week old female wild type mice (Table 1). Control mice, receiving LPS only, showed a series of responses, such as shivering, fever, lethargy, watery eyes, and ultimately death. These septic symptoms were less severe in mice treated with *Eclipta prostrata* L. Lower doses of *Eclipta prostrata* L. (25–50 mg/mouse) allowed mice to recover from initial septic shock symptoms.

TABLE 1

Inhibition of Septic Shock by *Eclipta prostrata* L. extract

|  | Day 1 | Day 2 | Day 3 |
|---|---|---|---|
| LPS alone | very sick | died | |
| EP 25 mg/mouse | not sick | not sick | |
| EP 50 mg/mouse | not sick | not sick | |
| LPS/EP 25 mg | sick | better | recovered |
| LPS/EP 50 mg | not as sick | slightly sick | recovered |

Since caspase-11 expression is highly induced by LPS stimulation, the induction of caspase-11 was examined in mice that had been injected with LPS (40 μg/g body weight) either with or without *Eclipta prostrata* L. extract. Four hours after injection, the mice were sacrificed and their spleens were removed and prepared for Western blot analysis. The Western blot was probed with an anti-caspase-11 monoclonal antibody. The results showed that *Eclipta prostrata* L. inhibited the induction of caspase-11 (FIG. 1). Thus, there is a component in Eclipta prostrata L. that acts to modulate the inflammatory response of LPS by inhibiting caspase-11 induction.

EXAMPLE 2

Identification of a Compound That Modulates Caspase-11 Expression

BalbC/3T3 cells treated with LPS (2 μg/ml) for 6 hours and then assayed for expression of caspase-11 protein by Western blot analysis revealed that LPS induces the expression of caspase-11 in this cell culture model. BalbC/3T3 cells were next preincubated with an ethanol extract of the plant *Eclipta prostrata* L. (454 g of *Eclipta prostrata* L. was extracted into 8 ml of ethanol; 5 μl of extract/ml of tissue culture media was applied to the cell culture) for 6 hours, followed by treatment with LPS for 6 hours, as described above. The level of caspase-11 protein expression was then measured. Western blot analysis of the lysates of cells receiving the ethanol extract and LPS, as described above, revealed that contact of the cells with the ethanol extract of *Eclipta prostrata* L. alone did not modulate the expression of caspase-11, nor did it suppress the induction of caspase-11 expression by LPS, as described above.

Figure 2:
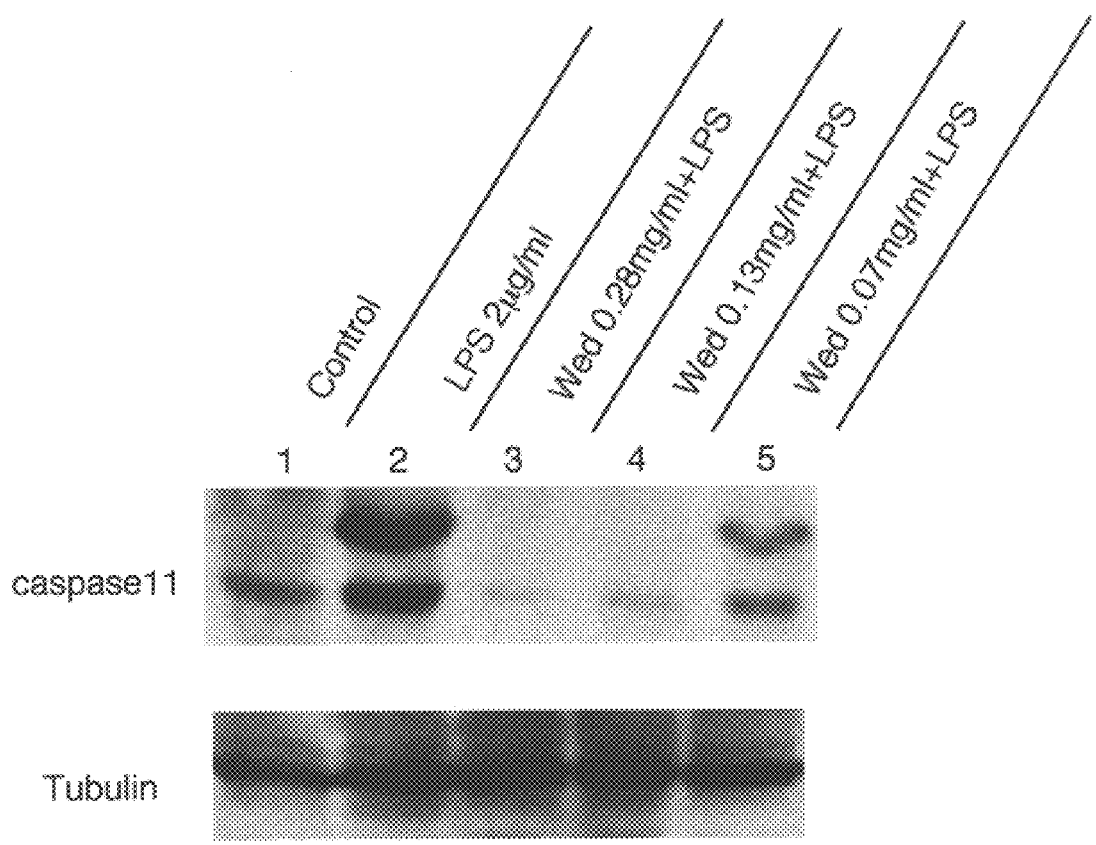
FIG. 2 is a scanned image of a Western blot showing the effects of wedelolactone on the LPS-induced expression of caspase-11. BalbC/3T3 cells were treated with varying concentrations of wedelolactone (Wed) for 6 hours and then treated with LPS for 6 hours. The expression of caspase-11 and tubulin (a control) in these samples and control samples (untreated cells and cells treated with LPS alone) were examined by Western blot analysis.

The ethanol fraction of *Eclipta prostrata* L. was then concentrated by evaporation. The dried ethanol extract was next washed with boiling water and the boiling water fraction, containing components of *Eclipta prostrata* L. that had dissolved into the boiling water, was partitioned with ethyl acetate. This ethyl acetate fraction, containing flavenoids and other secondary metabolites, did not induce the expression of caspase-11, but did suppress the induction of caspase-11 protein levels normally induced by LPS in BalbC/3T3 cells. In addition, the ethyl acetate fraction inhibited the expression of LPS-induced caspase-11 expression in a dose dependent manner (FIG. 2).

EXAMPLE 3

Inhibition of the NF-κB Pathway by the Active Ethylacetate Fraction of *Eclipta Prostrata* L.

Figure 3:
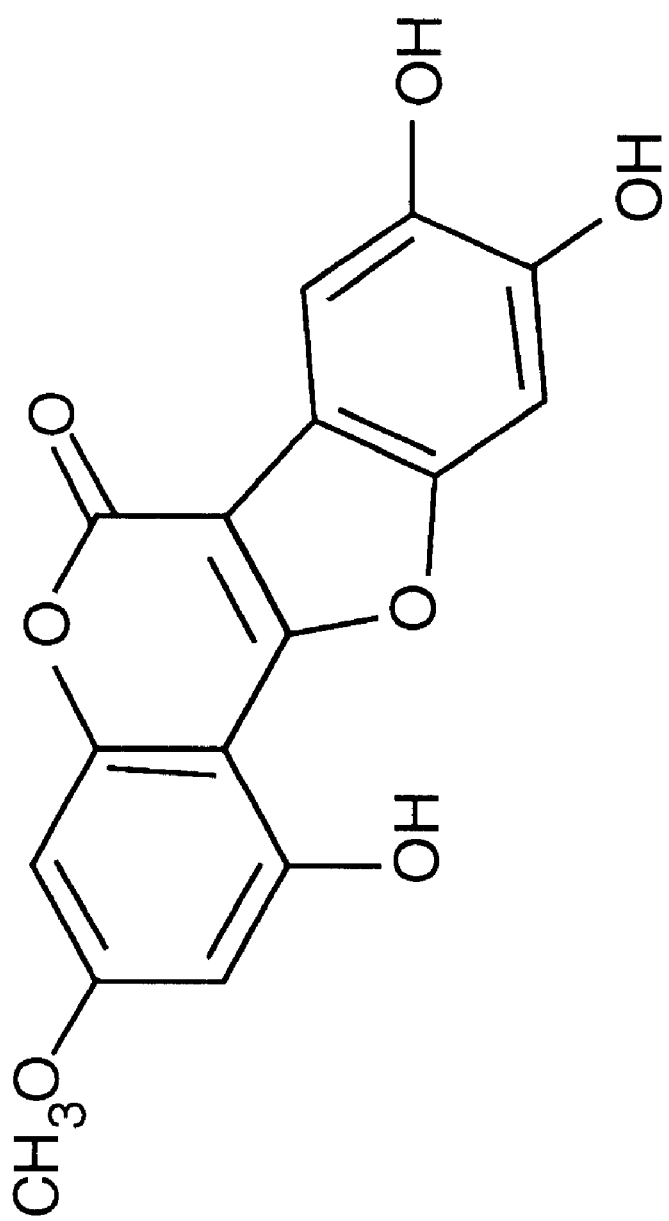
FIG. 3 is a schematic representation of the chemical structure of wedelolactone.
Figure 4:
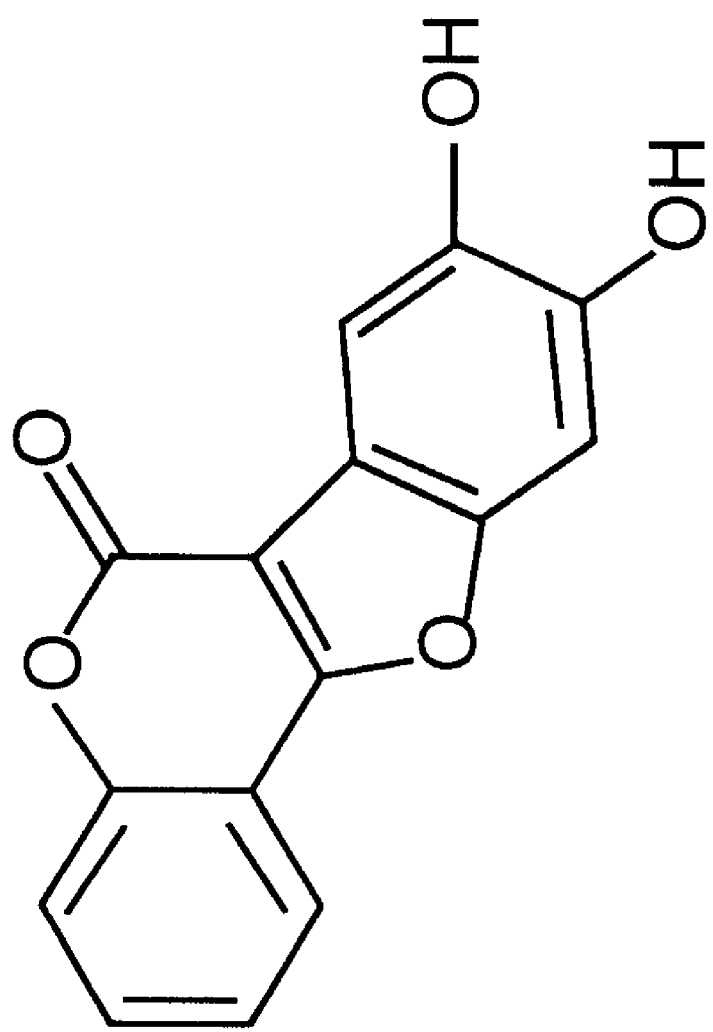
FIG. 4 is a schematic representation of the chemical structure of 11,12 dihydroxy coumestan.
Figure 5A:
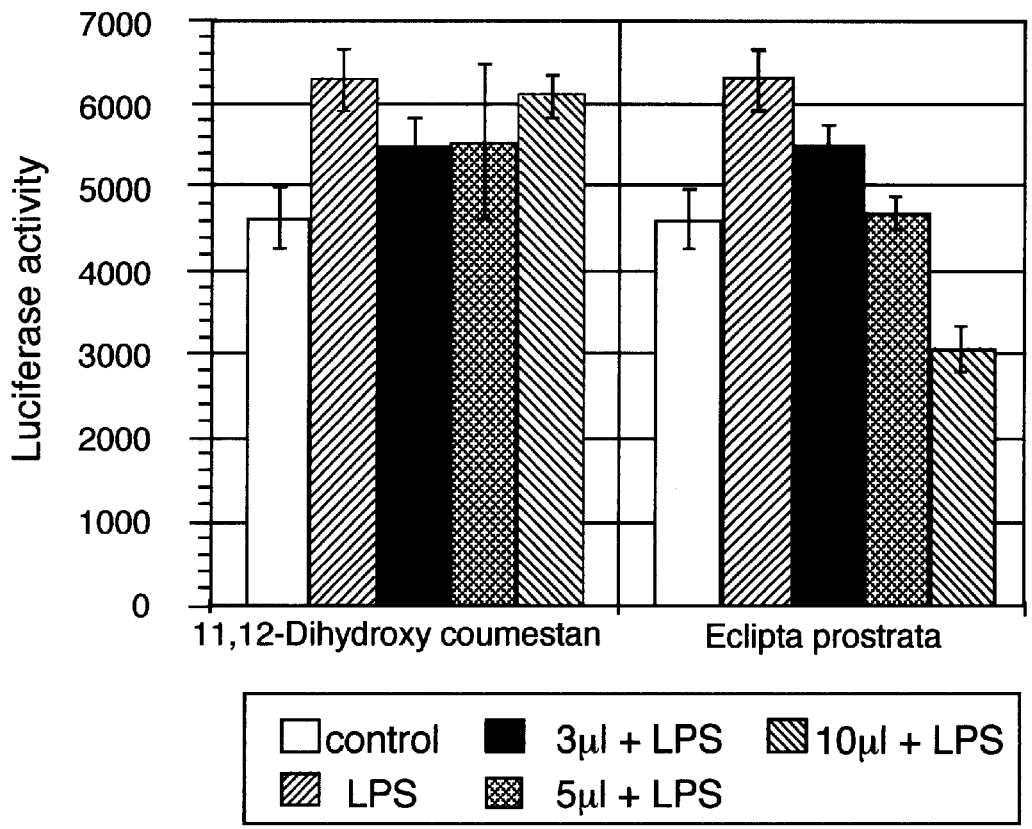
FIG. 5A is a graph of the effect of the active Eclipta prostrata L. fraction on induction of NF-κB and caspase-11. BalbC/3T3 cells were transfected with an NF-κB luciferase report construct and treated with the ethylacetate fraction of Eclipta prostrata L. ethylacetate extract (EA) or 11,12-dihydroxy coumestan (10 mg/ml) for 1 hour and then treated with 2 µg/ml LPS for 9 hours. Luciferase activity was then determined.
Figure 5B:
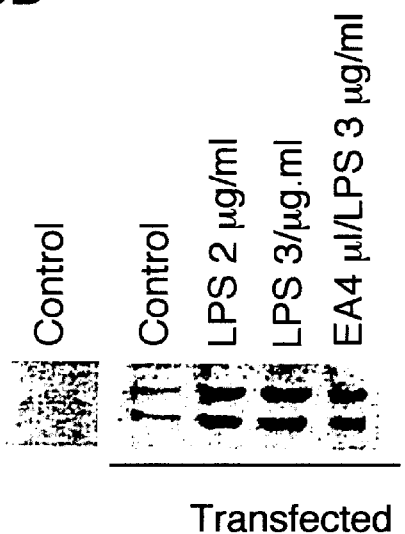
FIG. 5B is a scanned image of a Western blot analysis of the inhibition of caspase-11 induction by the ethylacetate fraction of Eclipta prostrata L. BalbC/3T3 cells were transfected with an NF-κB luciferase report construct and treated with the ethylacetate fraction of Eclipta prostrata L. ethylacetate extract (EA) or 11,12-dihydroxy coumestan (10 mg/ml) for 1 hour and then treated with 2 pg/ml LPS for 9 hours. Control and transfected lysates from cells with or without ethylacetate extract (EA) treatment were analyzed by Western blot using an anti-caspase-11 antibody.

Since caspase-11 is induced through the NF-κB pathway, wedelolactone (FIG. 3) may inhibit the activity of NF-κB. To examine this possibility, BalbC/3T3 cells were transfected with an NF-κB-luciferase reporter plasmid (containing an NF-κB response element). The cells were then treated with the ethylacetate fraction of *Eclipta prostrata* L. or 11,12-dihydroxy coumestan (a compound similar in structure to wedelolactone, but which does not inhibit caspase-11 expression) for 1 hour, and then treated with LPS for and additional 9 hours (FIG. 4). Although the transfection procedure appeared to induce NF-κB to a certain extent, treatment with LPS consistently induced further activation of NF-κB. The ethylacetate fraction of *Eclipta prostrata* L. inhibited the induction of NF-κB activity (FIG. 5A) and caspase-11 expression (FIG. 5B). 11,12-dihydroxy coumestan did not inhibit NF-κB induction. These data indicate that wedelolactone in the ethylacetate fraction of *Eclipta prostrata* L. specifically inhibits the induction of caspase-11 expression by inhibiting NF-κB activity.

Figure 6:
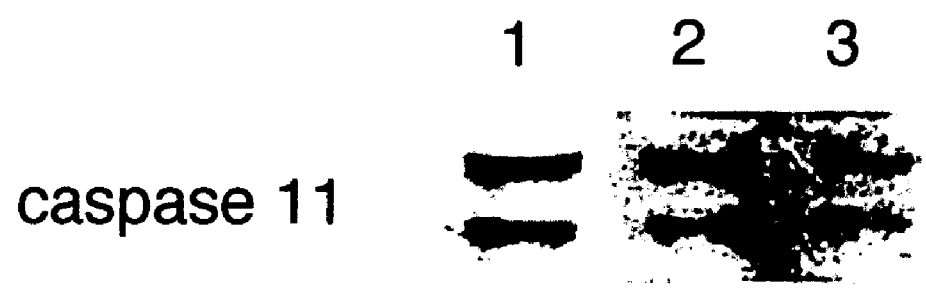
FIG. 6 is a scanned image of a Western blot analysis of the effect of the active ethylacetate fraction of Eclipta prostrata L. (Eclipta p.) on induction of caspase-11 by TNF-α. BalbC/3T3 cells were pre-treated with the active ethylacetate fraction for 1 hour and then with TNF-α for 6 hours. Lane 1: TNF-α 2 ng/ml. Lane 2: Ecliptap. 3 µl, TNF-2 ng/ml. Lane 3: Eclipta p. 5 µl, TNF-α 2 ng/ml. The amount of protein in each lane was normalized to tubulin staining (not shown).

TNF-α is an efficient activator of NF-κB. It acts by inducing the degradation of IκBα, the inhibitor of NF-κB (Mercurio et al., Oncogene 18, 6163–6171, 1999). To examine if the ethylacetate fraction of *Eclipta prostrata* L. can also inhibit the induction of caspase-11 expression induced by TNF-α BalbC/3T3 cells were treated with TNF-α with or without pretreatment with the ethylacetate fraction of *Eclipta prostrata* L. (FIG. 6). The induction of caspase-11 by TNF-α was also inhibited by treatment with the extract.

Figure 7:
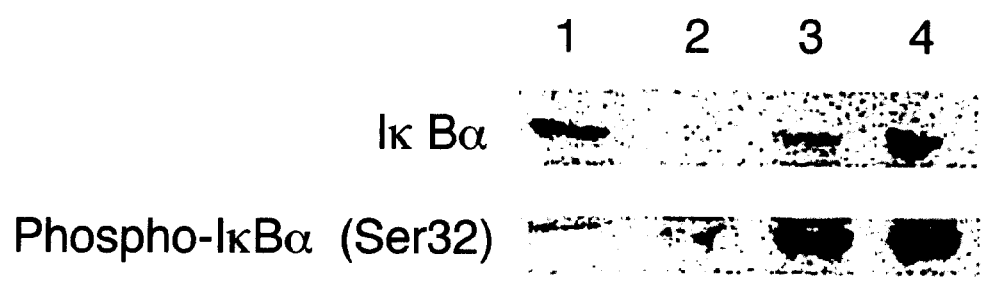
FIG. 7 is a scanned image of a Western blot analysis of the effect of the active ethylacetate fraction of Eclipta prostrata L (Eclipta p.) on the expression and phosphorylation of IκBα. BalbC/3T3 cells were pre-treated with the ethylacetate fraction of Eclipta prostrata L for 1 hour and were then treated with TNF-α for 5 minutes. Expression of IκBα and phospho-IκBα were examined by Western blot analysis, using an antibody that recognizes IκBα (top panel) or phospho-IκBα (Serine32) (bottom panel). The amount of protein in each lane was normalized to anti-tubulin staining (not shown). Lane 1: untreated control. Lane 2, TNF-α 2 ng/ml. Lane 3: Eclipta p. 3 µl, TNF-α 2ng/ml. Lane 4: Eclipta p. 5 µl, TNF-α 2 ng/ml.

To investigate the mechanism by which the extract inhibited the induction of caspase-11 by TNF-α, the level of IκBα protein, as well as its phosphorylation state were assayed. Treatment of the cells with *Eclipta prostrata* L. extract clearly inhibited the degradation of IκBα induced by TNF-α. The phosphorylation of IκBα at serine 32 and serine 36 by IκBα kinase, the signal to target IκBα for degradation, was not inhibited. Pretreatment of the cells with the ethylacetate fraction caused accumulation of the phosphorylated form of IκBα, as indicated by Western blot analysis using an antibody specific for phosphoserine 32 of IκBα (FIG. 7). This result indicates that the ethylacetate fraction of *Eclipta prostrata* L. inhibits NF-κB activity by inhibiting the degradation of IκBα downstream from IκBα kinase.

EXAMPLE 4

Purification of Wedelolactone

The ethyl acetate fraction of the above purification scheme, which contained the active ingredient that modulated expression of caspase-11 was further purified by silica gel chromatography and preparative high pressure liquid chromatography (HPLC) using a C18 column (15–100% acetonitrile liner gradient). HPLC (using the C18 column) and liquid chromatography-mass spectrometry (LC-Mass spectrometry) analyses of the purified ethyl acetate fraction showed that the fraction separated by preparative HPLC contains two major components showing UV absorptions. The components were acetylated and isolated using preparative thin layer chromatography (TLC). The structures of the two isolated components were then identified by LC-Mass spectrometry and nuclear magnetic resonance (NMR) techniques.

Each of the isolated components was then administered to the BalbC/3T3 cells, and examined for their ability to suppress the LPS-induced expression of caspase-11 protein levels. It was determined that a 6 hour pre-treatment of the cells with one of the components, wedelolactone (70 $\mu$g/ml; FIG. 3), suppressed caspase-11 expression in cells subsequently treated with LPS. These results demonstrate that wedelolactone can modulate the expression of caspase-11.

In addition, the ethanol extract fraction and the boiling water extract, each containing wedelolactone, also suppressed the expression of caspase-11. The suppression of caspase-11 expression by these fractions, was less than that of the ethyl acetate fraction of wedelolactone.

EXAMPLE 5

Synthesis of Wedelolactone and Structural Derivatives Thereof

As a final confirmation that wedelolactone is responsible for inhibiting caspase-11 induction in *Eclipta prostrata* L. extract and to further characterize the structural and functional relationship of wedelolactone, wedelolactone may be organically synthesized. Our approach to the synthesis of wedelolactone and structural derivatives of wedelolactone, for example, those shown in FIGS. 8 and 9, employs a similar conventional route described by Pandey et al. (supra) featuring tyrosinase oxidation of catechol (molecule 1 of FIG. 10) to synthesize the o-quinone (molecule 2 of FIG. 10) from catechol. The o-quinone reacts with different substituted 4-hydroxyl-coumarins (molecule 3 of FIG. 10) to give the wedelolactone related molecules (molecule 4 of FIG. 10).

Figure 11:
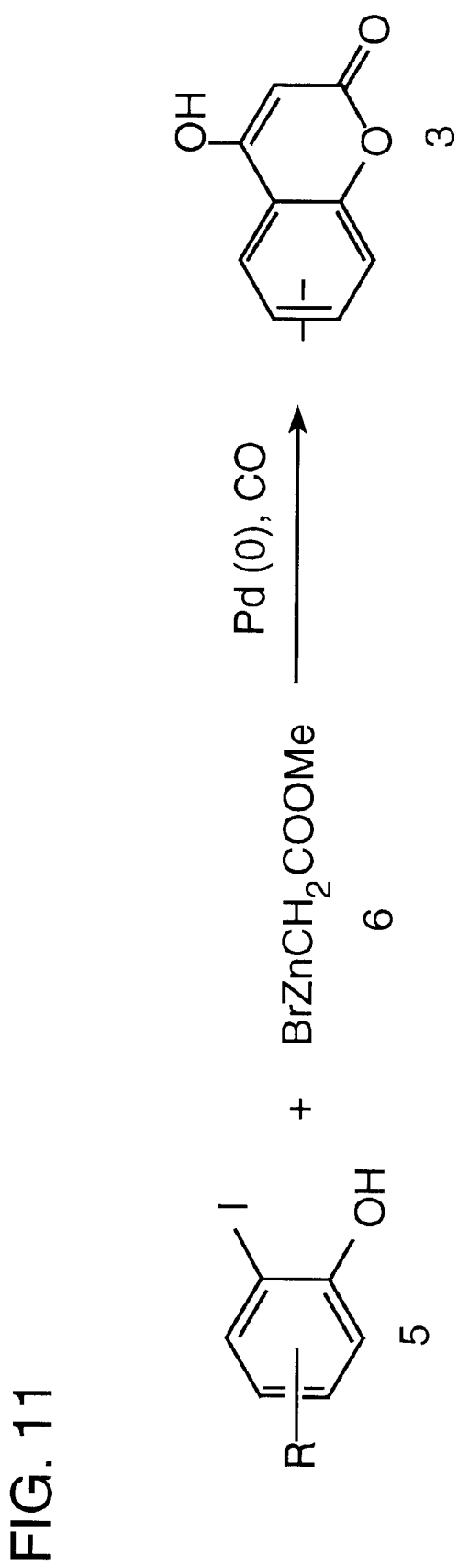
FIG. 11 is a schematic representation of steps involved in the synthesis of substituted 4-hydroxyl-coumarins. It is speculated that iodophenol (molecule 5) will undergo palladium catalyzed carbonylative cross-coupling with a Reformatsky reagent (molecule 6) to give substituted 4-hydroxyl-coumarin (molecule 3) in a one step operation.

Methods to synthesize substituted 4-hydroxyl-coumarins in order to make the combinatorial synthesis of wedelolactone feasible are shown in FIG. 11. It is proposed that iodophenol (molecule 5 of FIG. 11) undergoes palladium catalyzed carbonylative cross-coupling with a Reformatsky reagent (molecule 6 of FIG. 11) to give substituted 4-hydroxyl-coumarin in a one step operation.

In addition, a combinatorial approach is undertaken to generate structural derivatives of wedelolactone. Using this approach, a library of structural derivatives of wedelolactone is generated and analyzed for structure-activity relationships (SAR). The flexibility and efficiency of our approach for the solid-phase synthesis of wedelolactone allows the generation of a plethora of compounds with rather simple modifications of the original synthesis schemes.

The design of structural derivatives of wedelolactone is guided by novelty of structure and ease of chemical synthesis. The structural modifications of wedelolactone are mainly focused on the molecules of FIGS. 12 and 13.

Figure 8:
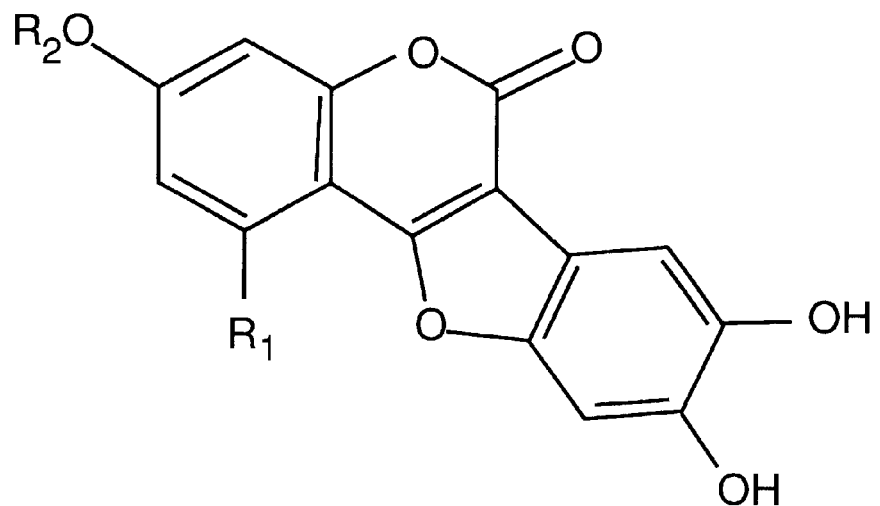
FIG. 8 is a schematic representation of the chemical structure of a compound that may be used to treat or prevent cell death or inflammation. In this representation, $R_1$ is hydrogen or a hydroxyl or methoxyl group, and $R_2$ is hydrogen or an alkyl group, for example, a methyl or ethyl group.
Figure 9:
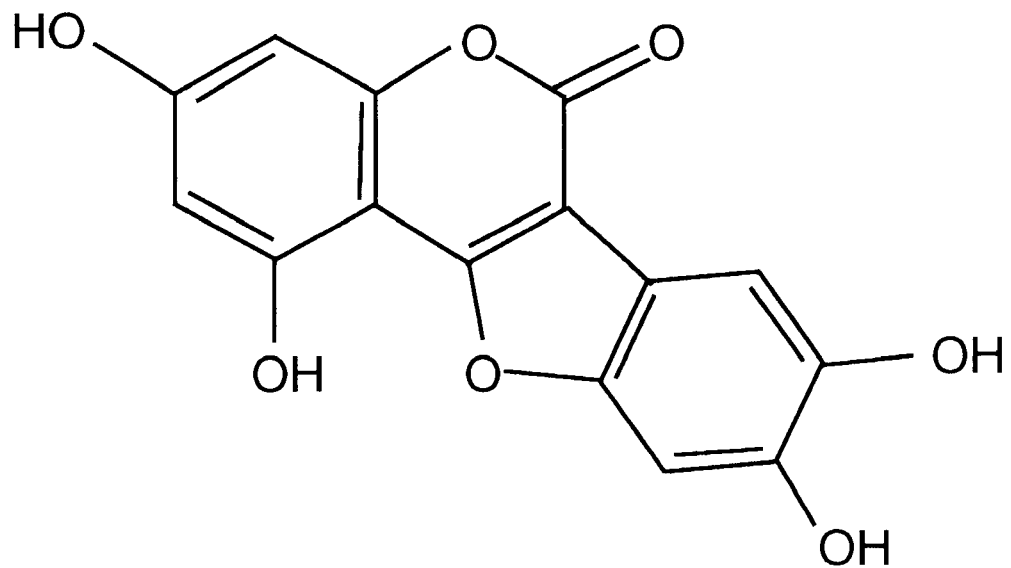
FIG. 9 is a schematic representation of the chemical structure of a compound that may be used to treat or prevent cell death or inflammation.
Figure 10:
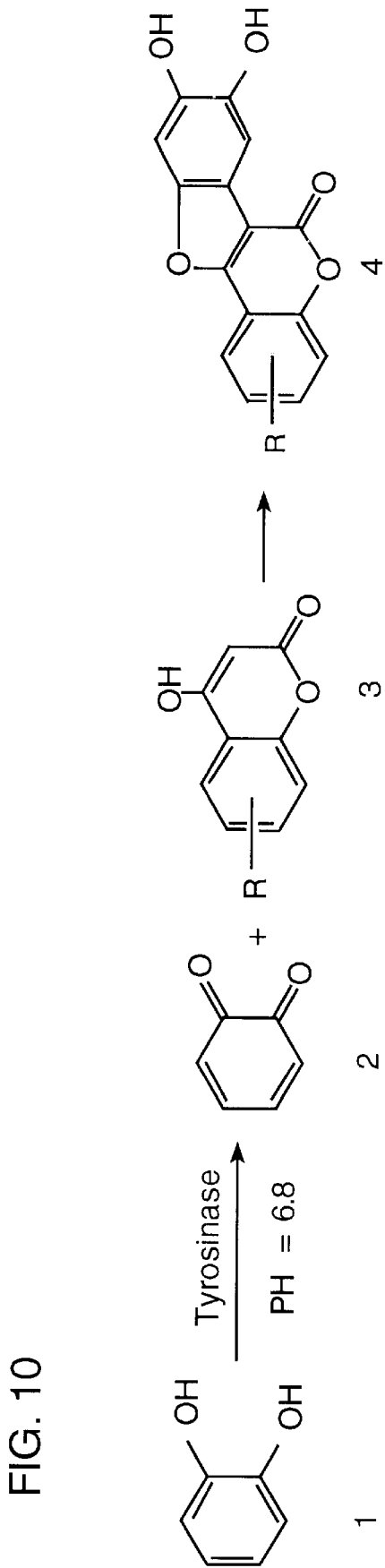
FIG. 10 is a schematic representation of the steps involved in the synthesis of structural derivatives of wedelolactone. In this representation, the synthesis begins with tyrosinase oxidation of catechol (molecule 1) to synthesize the o-quinone (molecule 2) from catechol. The o-quinone can react with different substituted 4-hydroxyl-coumarins (molecule 3) to give the wedelolactone related molecules (molecule 4).
Figure 12:
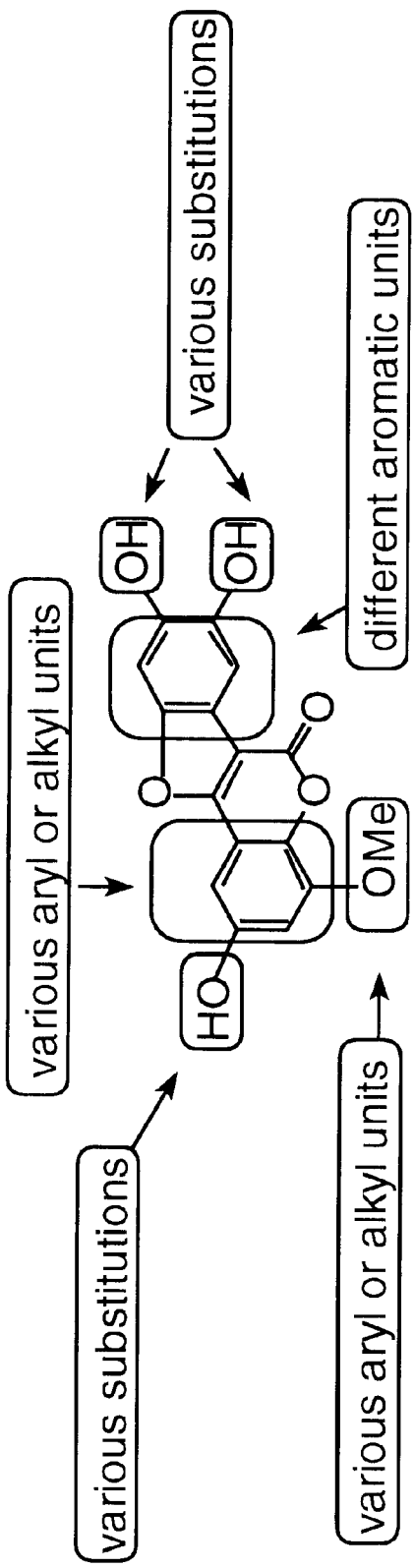
FIG. 12 is a schematic representation of substitutions that may be made to wedelolactone during the generation of a combinatorial library of structural derivatives of wedelolactone.
Figure 13:
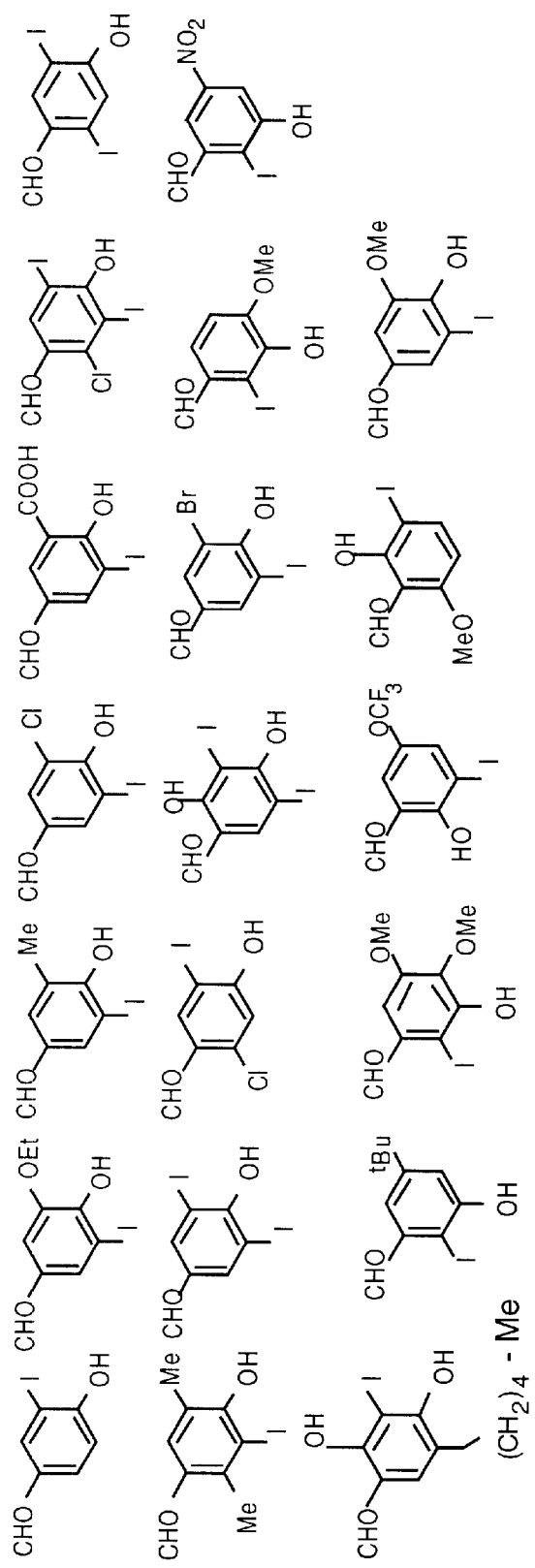
FIG. 13 is a schematic representation of iodophenol analogs that may be used to generate a combinatorial library of structural derivatives of wedelolactone.

FIG. 12 is a schematic representation of substitutions that are made to wedelolactone during the generation of a combinatorial library of structural derivatives of wedelolactone. To aid in the generation of such a library the iodophenol analogs shown in FIG. 13 are used to generate various substituted 4-hydroxyl-coumarins. Based on the information provided above, various wedelolactone analogs, for example, those shown in FIGS. 8 and 9, are synthesized and a large library is generated using the "split and mix" method, for example, as described by Furka et al. (Comb. Chem. High Throughput Screen 2:105–122, 1999).

Alternatively, a large number of analogs are made using conventional solution-phase chemistry, known to those of skill in the fields of organic and medicinal chemistry. Furthermore, the use of both solution-phase synthesis and combinatorial synthesis of structural derivatives of wedelolactone are used and integrated in the search for ideal mimics of wedelolactone that are more efficacious. The probability of finding interesting mimics of wedelolactone with improved pharmacological profiles from a large number of structural derivatives is quite high.

EXAMPLE 6

Synthesis of Wedelolactone

Wedelolactone and its structural derivatives were synthesized using the following preferable methods. Wedelolactone was synthesized according to the scheme shown in FIG. 14, and its synthesis is now described in detail.

Retrosynthetic Analysis Strategy

Figure 15:
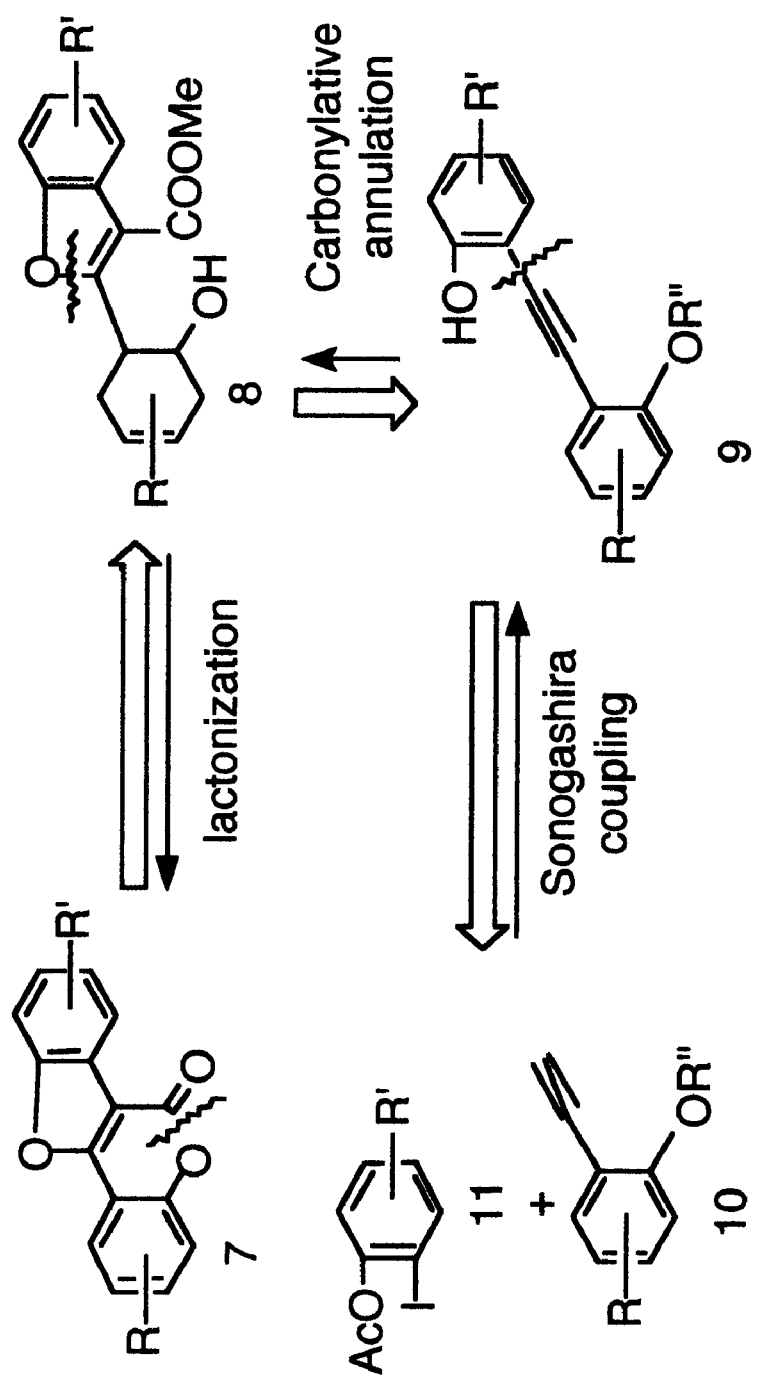
FIG. 15 is a schematic representation of the retrosynthetic analysis of wedelolactone's scaffold.

FIG. 15 outlines the proposed retrosynthetic analysis of wedelolactone's scaffold (molecule 7 of FIG. 15). The first disconnection of the six-membered ring lactone in molecule 7 reveals the 2-substituted methyl benzo[b]furan-3-carboxylate (molecule 8 of FIG. 15) as a precursor for synthesizing molecule 7. Further disconnection of the five-membered ring furan in molecule 8 leads to o-hydroxyl-phenylacetylene (molecule 9 of FIG. 15) as a starting material. Eventually, the o-hydroxyl-phenylacetylene (molecule 9) is constructed by a Sonogashra reaction from a substituted o-acetyl-iodobenzene (molecule 10 of FIG. 15) and phenylacetylene (molecule 11 of FIG. 15), respectively.

This approach toward the synthesis of wedelolactone is advantageous for a number of reasons: (1) a synthetic transformation from intermediate molecule 8 to 7 has been realized by Maeda et al., (Chem. Pharm. Bull. 42:2536, 1994); (2) an efficient new synthetic technology for the synthesis of 2-substituted methyl benzo[b]furan-3-carboxylate has been recently developed, as described herein; and (3) the starting materials of phenylacetylenes (molecule 10 of FIG. 15) and o-acetyl-iodophenols (molecule 11 of FIG. 15) are commercially available or easily synthetic accessible. Therefore, a variety of substituted methyl benzo[b]furan-3-carboxylates are obtained by this approach and a large number of analogs of wedelolactone are synthesized.

Total Synthesis of Wedelolactone

A program to systematically construct a 2,3-disubstituted benzo[b]furan library has been developed. One of the most difficult tests associated with the generation of a combinatorial library is the selection of proper reactions on a solid support. Although many reactions work very well in solution phase, some of them can not be utilized on a solid support due to the heterogeneous kinetic behavior of the library members on the solid support. In view of this fact, intermediate o-hydroxyl-arylacetylenes (molecule 12 of FIG. 16) were generated using a Sonogashira reaction as a key reaction, since this reaction has been extensively studied and was utilized successfully (Sonogashira et al., Tetrahedron Lett. 4467, 1975; Sonogashira, In Comprehensive Organic Synthesis, Trost and Fleming, Eds., Pergamon Press: New York, 1991, Vol. 3, P. 521; and Foley et al., J. Am. Chem. Soc. 121:9073–9087, 1999).

Figure 16:
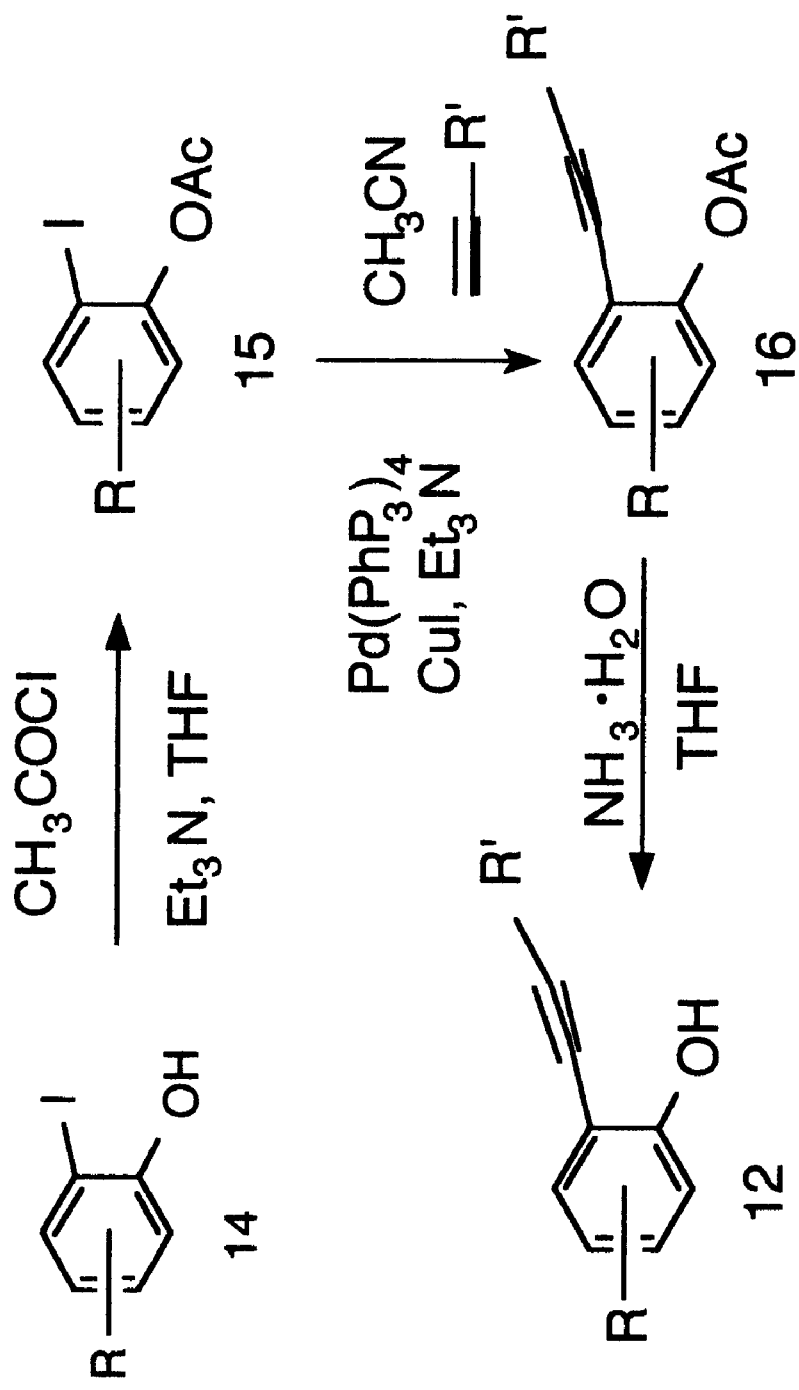
FIG. 16 is a schematic representation of the steps involved in the synthesis of intermediate molecule 12 by a Sonogashira reaction.

To generate the intermediate o-hydroxyl-arylacetylenes, iodophenol (molecule 14 of FIG. 16) was acetylated with acetyl chloride to give o-acetyl-iodobenzene (molecule 15 of FIG. 16), which reacted with acetylenes by a Sonogashira reaction to give o-acetyl-arylacetylenes (molecule 16 of FIG. 16). The intermediate (molecule 12 of FIG. 16) was obtained by hydrolysis of molecule 16 with ammonium hydroxide in tetrahydrofuran (THF) (FIG. 16).

Figure 17:
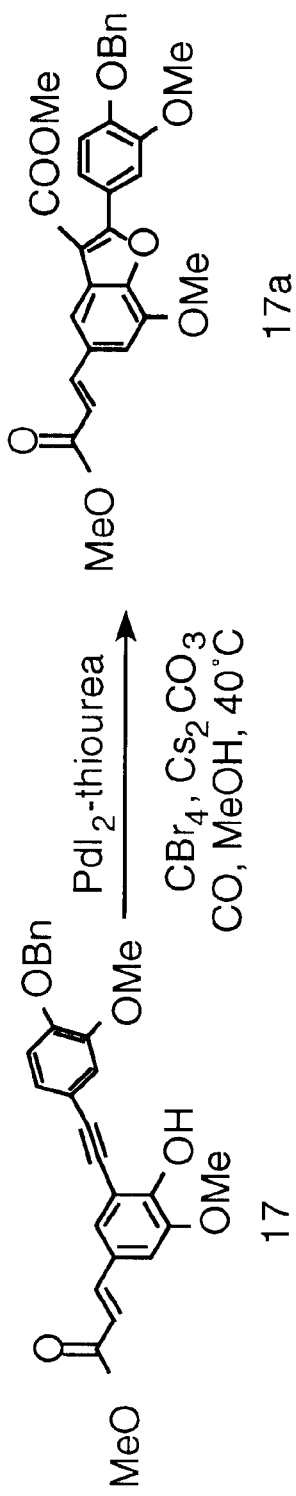

To generate substituted methyl benzo[b]furan-3-carboxylates, electron-deficient substrates, for example, molecule 17 of FIG. 17 were carbonylatively heteroannulated with $PdI_2$-thiourea, $CBr_4$ and $Cs_2CO_3$ as the base, in methanol at 40° C. and balloon pressure of CO, to give 84% yield of the desired product 17a of FIG. 17. The reaction was complete in less than 30 minutes. With each of the substrates (electron-rich and electron-deficient) the reaction gave satisfactory yields (Table 2) and went to completion in less than 30 minutes under the same conditions as described above. Furthermore, the tert-butyldimethylsilyl (TBS) protecting group (see entry 3 of Table 2) was found to be stable under this reaction condition.

Therefore, we have developed a highly effective co-catalysis system ($PdI_2$-thiourea, $CBr_4$) for carbonylative cyclization of both electron-deficient and electron-rich substrates of o-hydroxy-phenylacetylenes to the corresponding methyl benzo[b]furan-3-carboxylates; and, for the first time, we introduced carbon tetrabromide ($CBr_4$) as a superior oxidative agent for the turnover of palladium (0) to palladium (II). As a result, eight different methyl 2,3-disubstituted benzo[b]furan-3-carboxylates have been synthesized in solution phase and the yields are quite satisfactory (Table 2).

TABLE 2

Palladium-thiourea Catalyzed Carbonylative Annulation of o-hydroxy-arylacetylenes

| entry | o-hydroxyl phenylacetylene | carbonylative annulation product | yield |
|---|---|---|---|
| 1 | (structure) | (structure) | 84% |
| 2 | (structure) | (structure) | 81% |
| 3 | (structure) | (structure) | 85% |
| 4 | (structure) | (structure) | 80% |

TABLE 2-continued

Palladium-thiourea Catalyzed Carbonylative Annulation of o-hydroxy-arylacetylenes

| entry | o-hydroxyl phenylacetylene | carbonylative annulation product | yield |
|---|---|---|---|
| 5 | | | 78% |
| 6 | | | 84% |
| 7 | | | 80% |
| 8 | | | 79% |

2) Complete Synthesis of Wedelolactone

Figure 14:
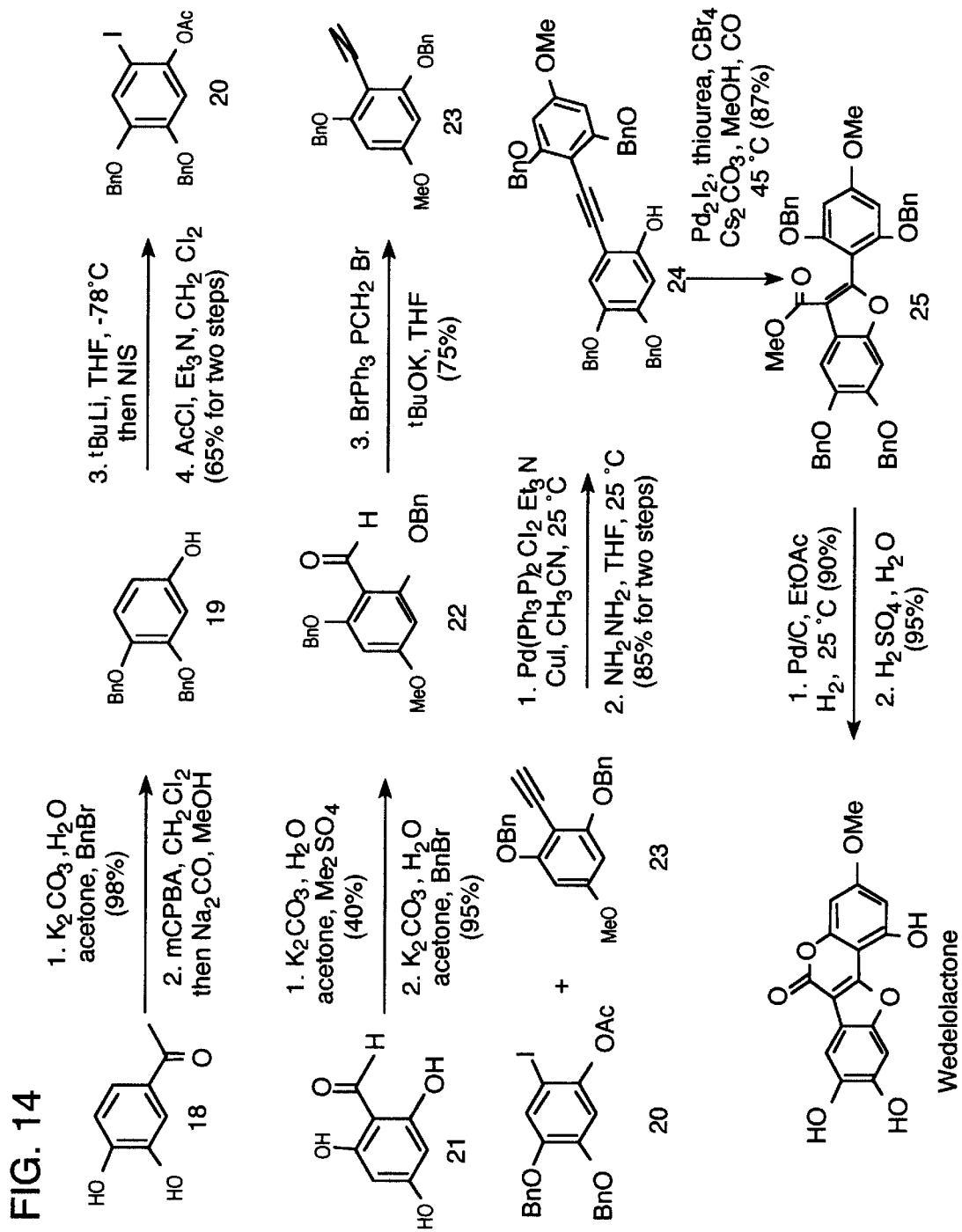
FIG. 14 is a schematic representation of the steps involved in the synthesis of wedelolactone.

To complete the synthesis of wedelolactone, two intermediates (molecules and 23 of FIG. 14) were constructed from compounds 18 and 21, respectively, of FIG. 14. Molecule 18 was first protected as dibenzyl ether, and then underwent Baeyer-Villiger oxidation, followed by hydrolysis to form molecule 19. The newly generated phenolic group of molecule 19 was utilized to direct the ortho-lithiation by treatment of compound 19 with n-BuLi in THF at −78° C., followed by reacting it with N-iodosuccinimide (NIS) to give the iodophenol (Edgar et al., J. Org. Chem. 55:5287,1990), which was then reacted with acetyl chloride in the presence of triethylamine to afford iodophenol acetate (molecule 20 of FIG. 14).

Molecule 21 of FIG. 14 was methylated with $Me_2SO_4$ under basic conditions to yield methyl ether, followed by dibenzylation with BnBr to generate molecule 22 of FIG. 14. Intermediate molecule 23 of FIG. 14 was generated by treatment of the corresponding aldehyde of molecule 22 with $BrPh_3CH_2Br$ in THF, using $^tBuOK$ as a base (Matsumoto et al., Tetrahedron Lett. 21: 4021, 1980; and Pianetti et al., Tetrahedron Lett. 27:5853, 1986).

The total synthesis of wedelolactone was completed by first coupling intermediate molecules 20 and 23 of FIG. 14, followed by acetyl deprotection with $NH_2NH_2$ to give molecule 24 of FIG. 14, which underwent palladium-catalyzed carbonylative annulation to form 2,3-disubstituted benzo[b]furan (molecule 25 of FIG. 14). Molecule 25 was then subjected to hydrogenation (to remove the benzyl protecting groups) and acid promoted lactonization, generating the final product, wedelolactone.

EXAMPLE 7

SAR Study of Wedelolactone

Since wedelolactone was successfully synthesized, the next step is to systematically evaluate the effects of substitution groups and scaffolds of wedelolactone for the inhibition of caspase-11 biological activity, NF-κB induction, cell death, and inflammation. To do so, wedelolactone's analogs, represented as the scaffolds of I, II, III and IV of FIG. 18 were synthesized.

To carry out the SAR study, the properly substituted polyphenol rings (FIG. 19), which represent A and D rings in wedelolactone (FIG. 18; structure I) are used to synthesize a series of substituted polyphenol based wedelolactones. Other substitutes (such as electron-withdrawing or electron-donating groups) to replace the phenols can also be used.

Once a position that is not critical for maintenance of the biological activity of the molecule is identified, this position is used to link it with an affinity reagent for purification of the wedelolactone target in a cell. A $^{13}$C-labeled wedelolactone (by using $^{13}$C-lableled carbon monoxide to perform palladium-catalyzed carbonylative annulation) can also be synthesized for structural and conformational studies of wedelolactone with its binding protein, employing NMR techniques.

Figure 18:
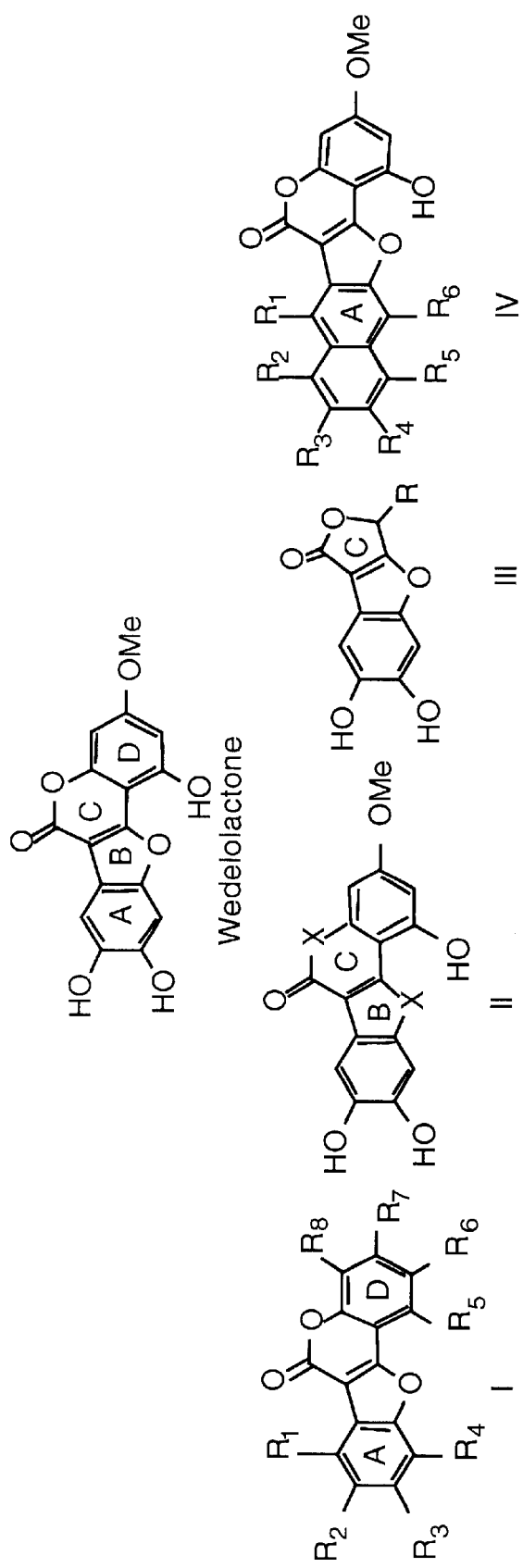
FIG. 18 is a schematic representation of analogs of wedelolactone, for use in SAR studies.
Figure 19:
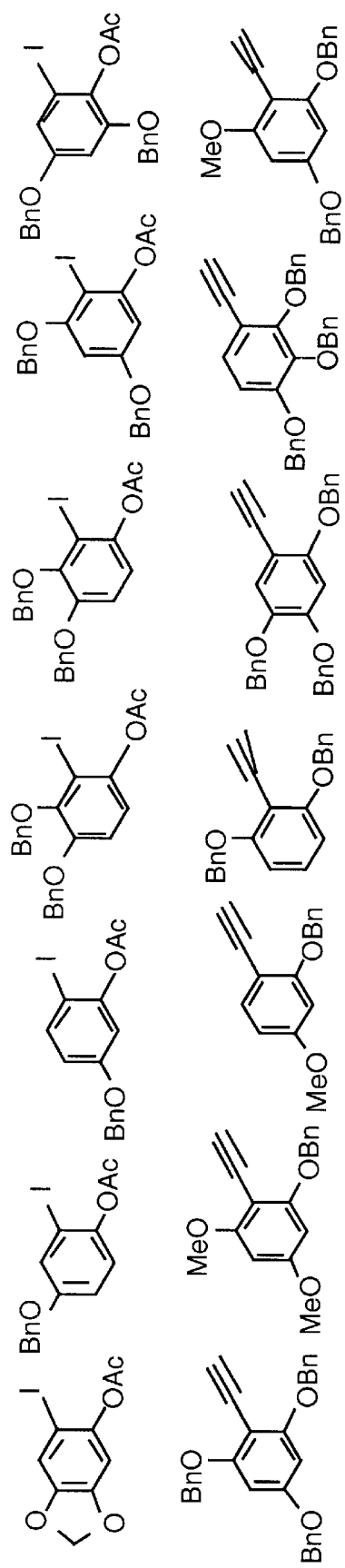
FIG. 19 is a schematic representation of polyphenol based wedelolactone analogs substrates, for use in SAR studies.
Figure 20:
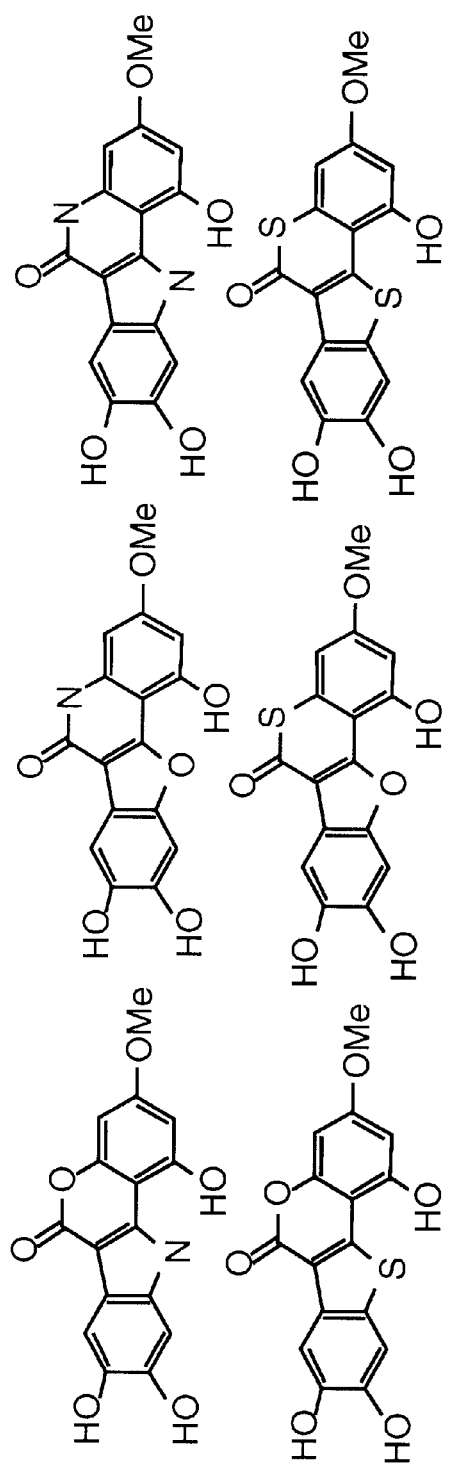
FIG. 20 is a schematic representation of nitrogen and sulfur based wedelolactone analogs substrates, for use in SAR studies.

In structure II of FIG. 18, the heteroatom X is changed from oxygen to nitrogen or sulfur (FIG. 20) to study the effects of these heteroatoms on caspase-11 biological activity, NF-κB induction, cell death, and inflammation.

Figure 21:
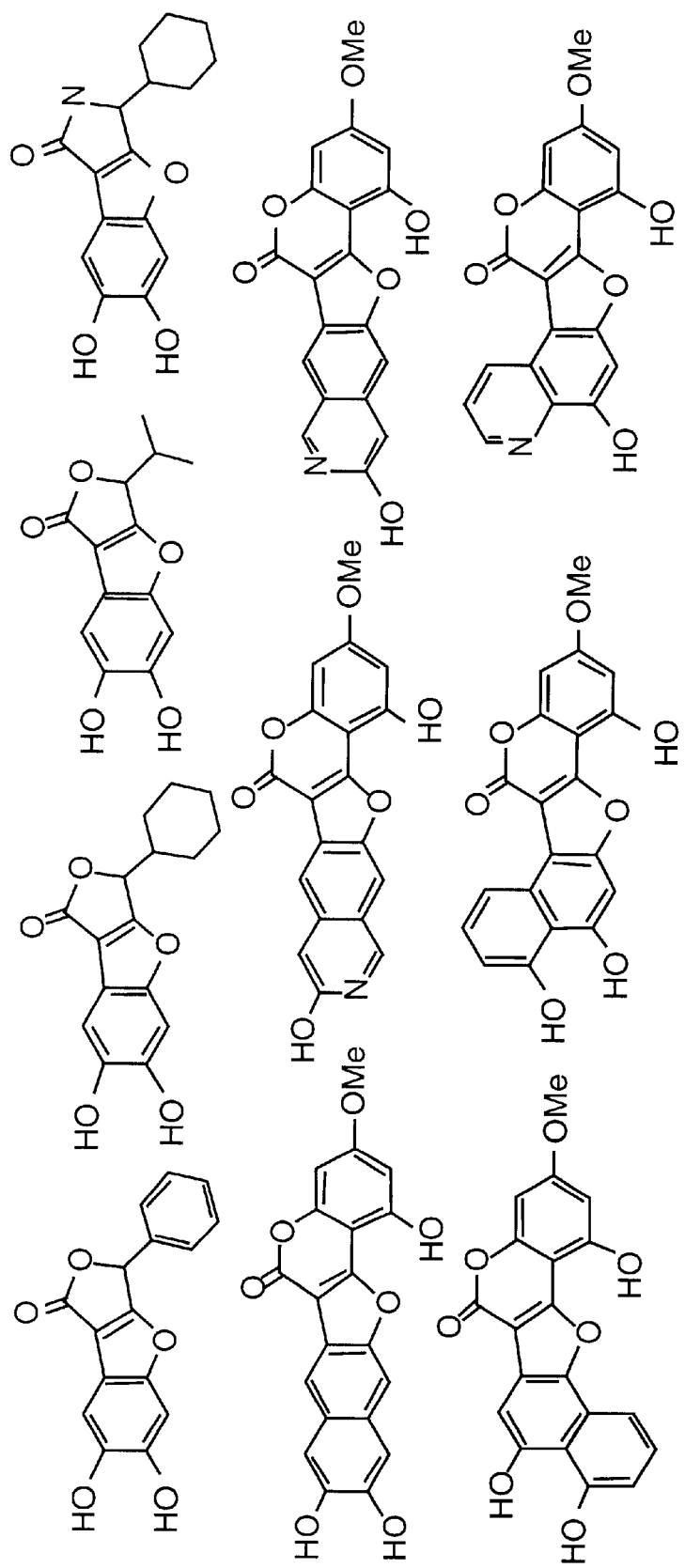
FIG. 21 is a schematic representation of the scaffolds of wedelolactone analogs that maintain the integrity of benzofuran or coumarin, for use in SAR studies.

To investigate the relationship between the biological activity and benzofuran or coumarin moieties of wedelolactone, the scaffolds that maintain the integrities of benzofuran and coumarin (FIG. 21), respectively, are synthesized for the testing of their effects on caspase-11 biological activity, NF-κB induction, cell death, and inflammation.

The SAR analysis described above allows for the determination of an insensitive region on wedelolactone for modification. The original functional group in this region, or a synthetically attached functional group, is used to connect it to a properly selected linker, where it is then immobilized on a matrix. Different types of matrix, such as affigel10, agarose beads, latex beads and Fractogel matrix are tested for affinity screening, in order to find out the best matrix for affinity chromatography.

EXAMPLE 8

Combinatorial Synthesis of Wedelolactone Derivatives on Solid Phase

In addition to the SAR analysis of the target molecule, new solid-phase synthetic technology is used for wedelolactone's library. A combinatorial approach allows for the preparation a large number of structurally diverse molecules for screening and SAR studies. FIG. 12 shows the structural diversity of wedelolactone's library.

Synthetic Study of Palladium-catalyzed Carbonylative Annulation on a Solid Support At the present time, the most commonly used resins in solid phase synthesis are polystyrene-based resins, such as graft copolymers of polystyrene (PS) and polyethylene glycol (PEG). Normally on polystyrene type resins, the functionality is directly attached at the aromatic ring (e.g., carboxylated polystyrene) or by way of a benzyl function, such as those used in chloromethylated or aminomethylated polystyrene derivatives. This benzyl derivative suffers in various aspects. For example, the benzyl linkage is not stable under the harsh acidic conditions often used in solid phase organic synthesis. In addition, the reactive sites are located directly on the polymer matrix, resulting in non-homogenous kinetic behavior. Tental Gel resin, a PEG-PS graft co-polymer, was developed to overcome the shortcomings of benzyl type polystyrenes. PEG, however, may modify the chemical behavior of the resin, and therefore, some applications of PEG may interrupt the reactions that are applied on the resin. In addition, since some strong Lewis acids interact with the ether bonds of the PEG resin, PEG resin can have a chelating effect on metals.

Figure 22:
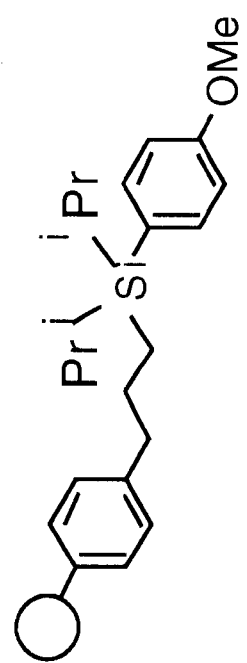
FIG. 22 is a schematic representation of two types of silyl linkers, and amide based silyl and an all carbon silyl linker, for the solid phase synthesis of derivatives of wedelolactone.
Figure 22:
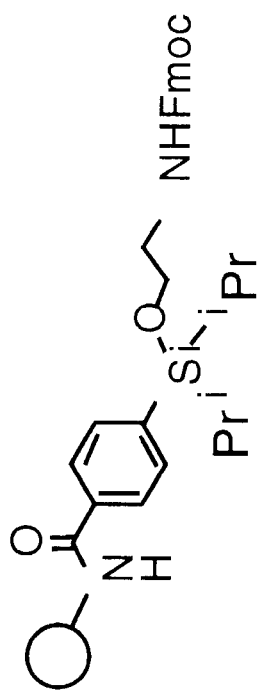

To overcome the shortcomings of benzyl type polystyrene resins, spacers have been developed and utilized to attach molecules to PS beads. In particular, the all carbon silyl linker not only improves the chemical homogeneity and kinetic rates, but also allows efficient high throughput screening of compounds (Plunkett et al., J. Org. Chem. 60:6006, 1995; Chenera et al., J. Am. Chem. Soc. 117:11999, 1995; Boehm et al., J. Org. Chem. 61:6498, 1996); Han et al., Tetrahedron Lett. 37:2703, 1996; Willems, Drug Discovery Today 2:214, 1997; Brown et al., J. Org. Chem. 62:7076,1997; Newlander et al., J. Org. Chem. 62:6726, 1997; Plunkett et al., J. Org. Chem. 62:2885, 1997; Hone et al., Tetrahedron Lett. 39:897, 1998; and Hu et al., J. Org. Chem. 63:4518, 1998). Therefore, our solid support employs the silyl linker based polystyrene beads (preferably an amide based silyl linker (molecule 28 of FIG. 22) and an all carbon silyl linker (molecule 29 of FIG. 22)) for the designed libraries so that the linker will be compatible with the selected reaction conditions of the screen.

Another important factor to consider in combinatorial synthesis is bead size. Polystyrene beads are commercially available in diameter sizes ranging from 1–750 microns. Reaction kinetics are generally faster using smaller beads, due to the higher surface area to volume ratio. In practice, however, small beads can lead to extended filtration times and lower loading ability.

Combinatorial synthesis on 400 or 500 micron PS beads, through the attachment of silyl linkers, results in compounds generated on the beads that can be released by treatment with HF pyridine, followed by methoxytrimethylsilane (TMSOMe). The unique features of using a large bead combinatorial strategy are: (1) the high loading capability of single bead; (2) on any individual bead of the solid support, only one compound is formed; and (3) the feasibility of high-throughput screening based on a one well per-bead method.

Figure 23:
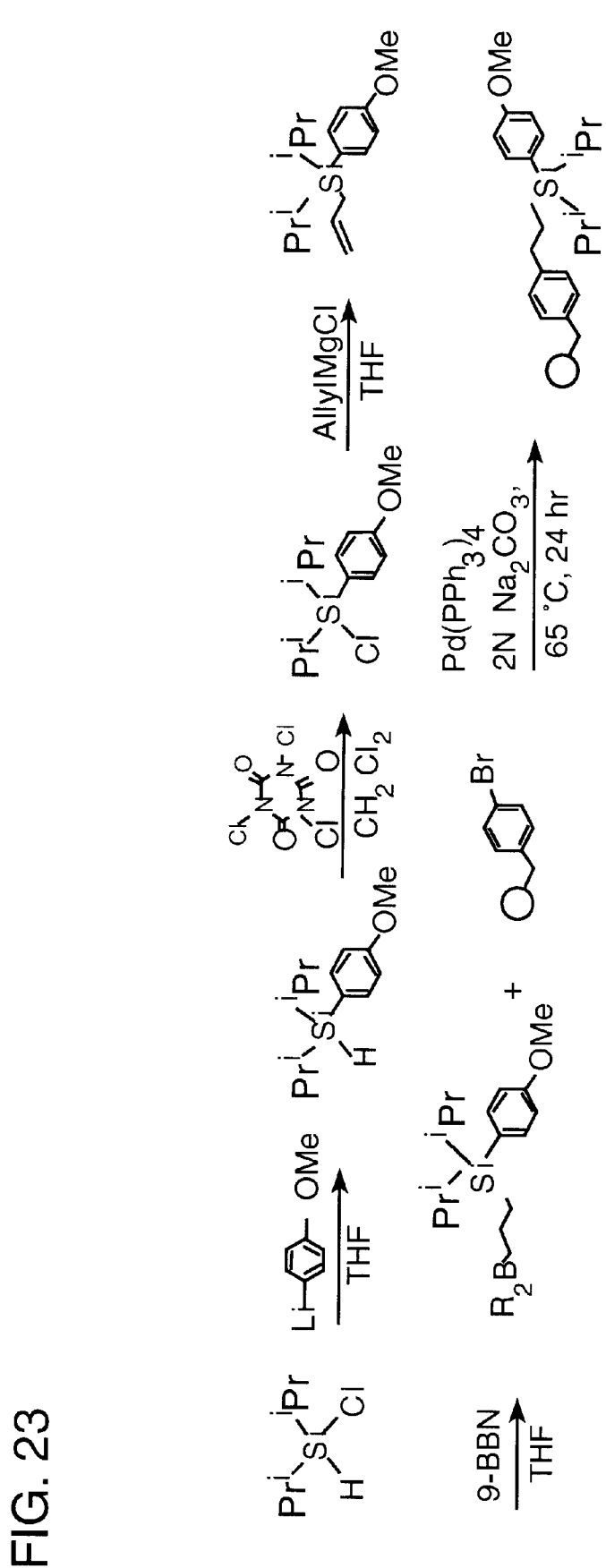
FIG. 23 is a schematic representation of the steps involved in the synthesis of an all carbon silyl linker on 400 and 500 micron polystyrene beads.

An all carbon silyl linker has been generated according to the methods of Woolard et al. (J. Org. Chem. 62:6102, 1997), by replacing the dimethyl groups to diisopropyl groups in order to increase the silyl linker stability. These synthetic transformations are illustrated in FIG. 23.

Figure 24:
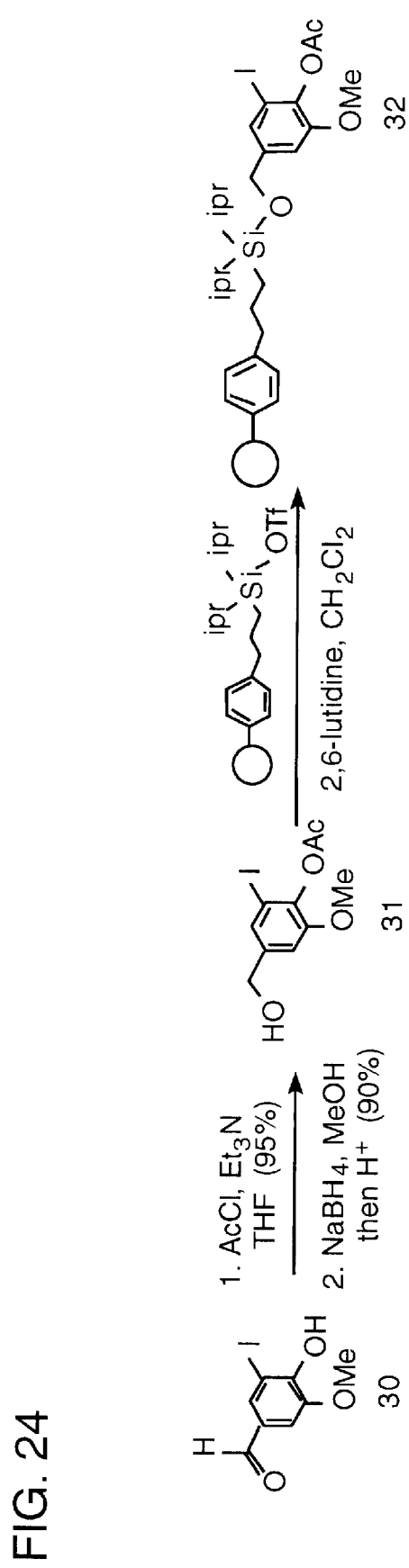
FIG. 24 is a schematic representation of the steps involved in the synthesis of substituted o-acetyl iodidebenzene on a polystyrene bead using an all carbon silyl linker.

Efficient solution phase chemistries for the synthesis of methyl benzo[b]furan-3-carboxylates, can also be applied to a solid support. To accomplish this application, iodophenol (molecule 31 of FIG. 24) was selected as a template to demonstrate this reaction. Compound 30 of FIG. 24 was first converted into an acetate, followed by reduction of the aldehyde into a primary alcohol to give molecule 31 of FIG. 24, which was immobilized on 500 Micron PS beads using an all carbon silicon linker to give o-acetyl iodobenzene (molecule 32 of FIG. 24).

Figure 25:
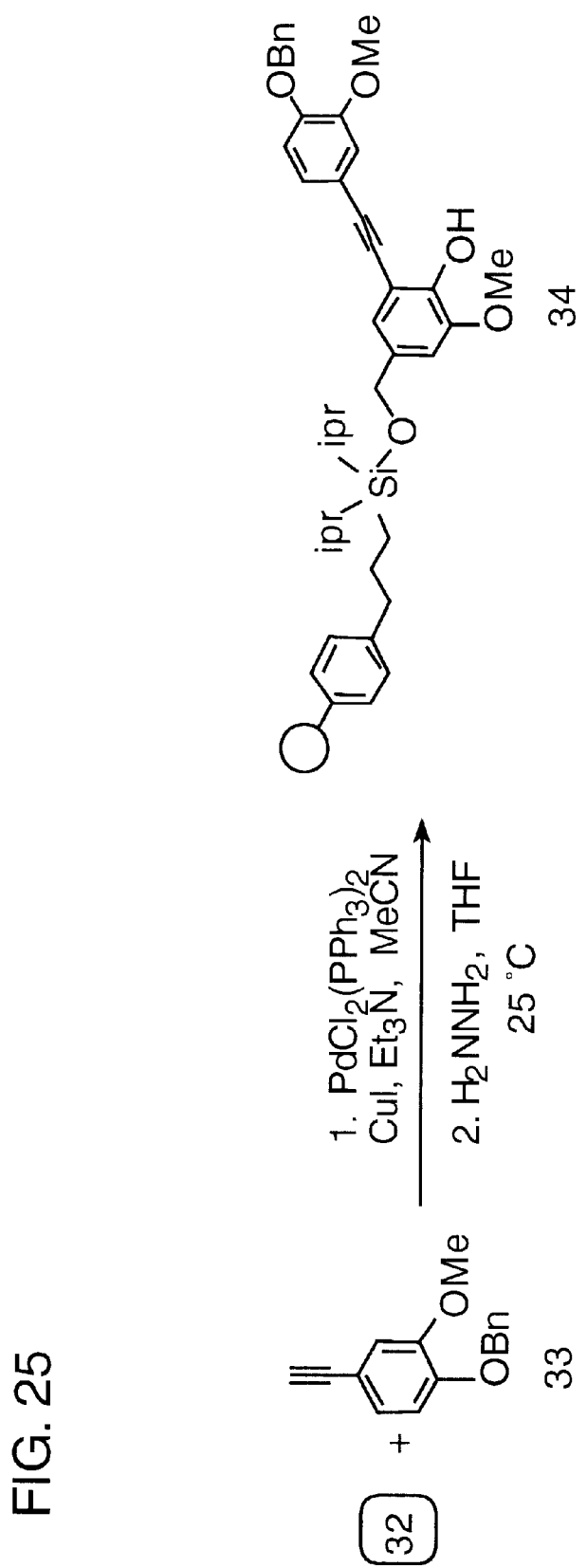
FIG. 25 is a schematic representation of the steps involved in the solid-phase synthesis of o-hydroxyl-phenylacetylene.

The o-acetyl iodobenzene was then coupled with acetylene (molecule 33 of FIG. 25) to give phenylacetylene by a Sonogashira reaction, followed by treatment with hydrizine (1.0 M) in THF to give the molecule 34 of FIG. 25. This molecule is then utilized for the synthesis of benzo[b]furan-3-carboxylate on a solid support. On bead high-resolution magic angle spinning NMR analysis and off-bead LC-MS and $^1$H-NMR studies indicated that very high purity of intermediate molecule 34 was obtained. Extensive investigation for this type of cross-coupling have been done, and the results are summarized in Table 3.

TABLE 2

Sonogashira Cross-coupling Reaction Between the On-bead Aromatic Iodide 32 with Various Terminal Acetylenes

| entry | RX | coupling product | conversion/purity[a] |
|---|---|---|---|
| 1 | 2-iodothiophene | Ar—≡—(2-thienyl) | >90% |
| 2 | 4-iodonitrobenzene | Ar—≡—C$_6$H$_4$—NO$_2$ | >95% |
| 3 | 4-iodo(trifluoromethyl)benzene | Ar—≡—C$_6$H$_4$—CF$_3$ | >95% |
| 4 | 3-iodoanisole | Ar—≡—C$_6$H$_4$—OMe (meta) | >95% |
| 5 | 4-iodoanisole | Ar—≡—C$_6$H$_4$—OMe (para) | >95% |
| 6 | 1-iodonaphthalene | Ar—≡—(1-naphthyl) | >85% |
| 7 | iodobenzene | Ar—≡—C$_6$H$_5$ | >90% |
| 8 | 4-iodotoluene | Ar—≡—C$_6$H$_4$—CH$_3$ | >90% |
| 9 | 4-iodo-n-butylbenzene | Ar—≡—C$_6$H$_4$—nBu | >90% |
| 10 | β-bromostyrene | Ar—≡—CH$_2$—C$_6$H$_5$ | >90% |
| 11 | 4-iodoacetophenone | Ar—≡—C$_6$H$_4$—C(O)CH$_3$ | >97% |

TABLE 2-continued

Sonogashira Cross-coupling Reaction Between the On-bead Aromatic
Iodide 32 with Various Terminal Acetylenes

| entry | H—≡—R | product | conversion/purity[a] |
|---|---|---|---|
| 12 | ethyl 2-(triflyloxy)cyclohex-1-ene-1-carboxylate | Ar—≡— (cyclopentene ethyl ester) | >94% |
| 1 | HC≡C-CH2-N(Me)-CH2-Ph | Ar-C≡C-CH2-N(Me)-CH2-Ph | >95% |
| 2 | HC≡C-N(nBu)2 | Ar-C≡C-N(nBu)2 | >95% |
| 3 | HC≡C-(CH2)3-CN | Ar-C≡C-(CH2)3-CN | >95% |
| 4 | HC≡C-(CH2)3-Cl | Ar-C≡C-(CH2)3-Cl | >95% |
| 5 | HC≡C-CH2-OC(O)CH3 | Ar-C≡C-CH2-OC(O)CH3 | >95% |
| 6 | HC≡C-CH(OH)-CH(CH3)2 | Ar-C≡C-CH(OH)-CH(CH3)2 | >95% |
| 7 | HC≡C-C(OH)(cyclopentyl) | Ar-C≡C-C(OH)(cyclopentyl) | >95% |
| 8 | HC≡C-C(OH)(cyclohexyl) | Ar-C≡C-C(OH)(cyclohexyl) | >95% |
| 9 | HC≡C-C(NH2)(cyclohexyl) | Ar-C≡C-C(NH2)(cyclohexyl) | >95% |
| 10 | HC≡C-Ph | Ar-C≡C-Ph | >95% |
| 11 | HC≡C-(CH2)3-OSMe3 | Ar-C≡C-(CH2)3-OH | >95% |

TABLE 2-continued

Sonogashira Cross-coupling Reaction Between the On-bead Aromatic
Iodide 32 with Various Terminal Acetylenes

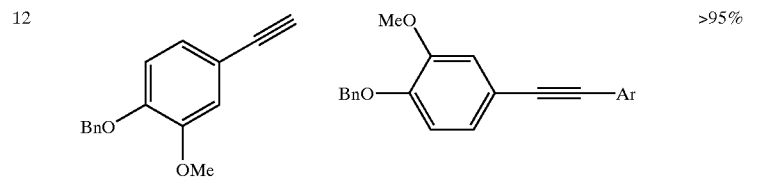

12                >95%

Figure 26:
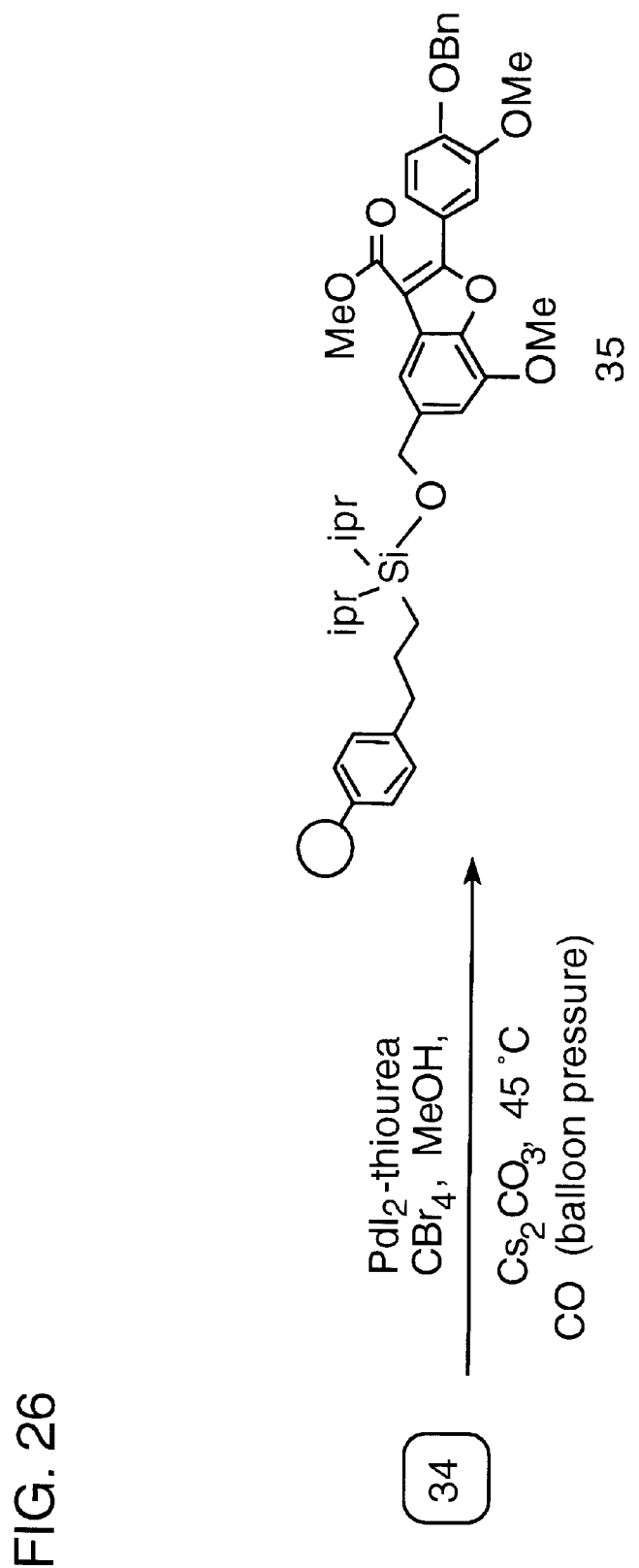
FIG. 26 is a schematic representation of the steps involved in the solid-phase synthesis of methyl 2,3-disubstituted benzo[b]faran-3-carboxylate.

[a]conversion and purity were obtained by calculating the individual integration of the corresponding NMR peak By using the on bead o-hydroxyl-phenylacetylene (molecule 34 of FIG. 26) as a template, the palladium-catalyzed carbonylative annulation method (to construct methyl benzo[b]furan-3-carboxylate (molecule 35 of FIG. 26)) was tested. The result was as good as in solution phase. To verify this reaction, all the substrates listed in Table 3 underwent the same type of carbonylative annulation, and more than 80% yields of desired benzo[b]furan-3-carboxylates were obtained.

Split-pool synthesis provides the theoretical means to synthesize the full matrix of every combination of building blocks in a multi-step synthesis. It also generates formidable analytical challenges. An important consequence of using a split-pool approach to synthesizing a library is the need for a code that allows for the identification of the compound on the bead. This is necessary because the amounts of compound made on each bead are too small for direct structure determination. A validation protocol to ascertain that a complex split-pool synthesis of encoded molecules yields the anticipated products in high purity and efficiency on a solid phase is designed as follows.

First, 2 to 3 small test libraries (containing approximately 200–300 members) are built to verify that the building blocks selected are efficiently incorporated into each step of the library synthesis. These products are characterized by HR-FAB-MS, LC-MS, and $^1$H-NMR, to ascertain that each of the members of the proposed library are made. Next, an encoding technology is applied to our library synthesis, using, in effect, a "bar code" to mark the beads with information that allows for the determination of which chemical steps it has undergone.

EXAMPLE 9

Biological Activity of Synthetic Wedelolactone in Vitro

Figure 27:
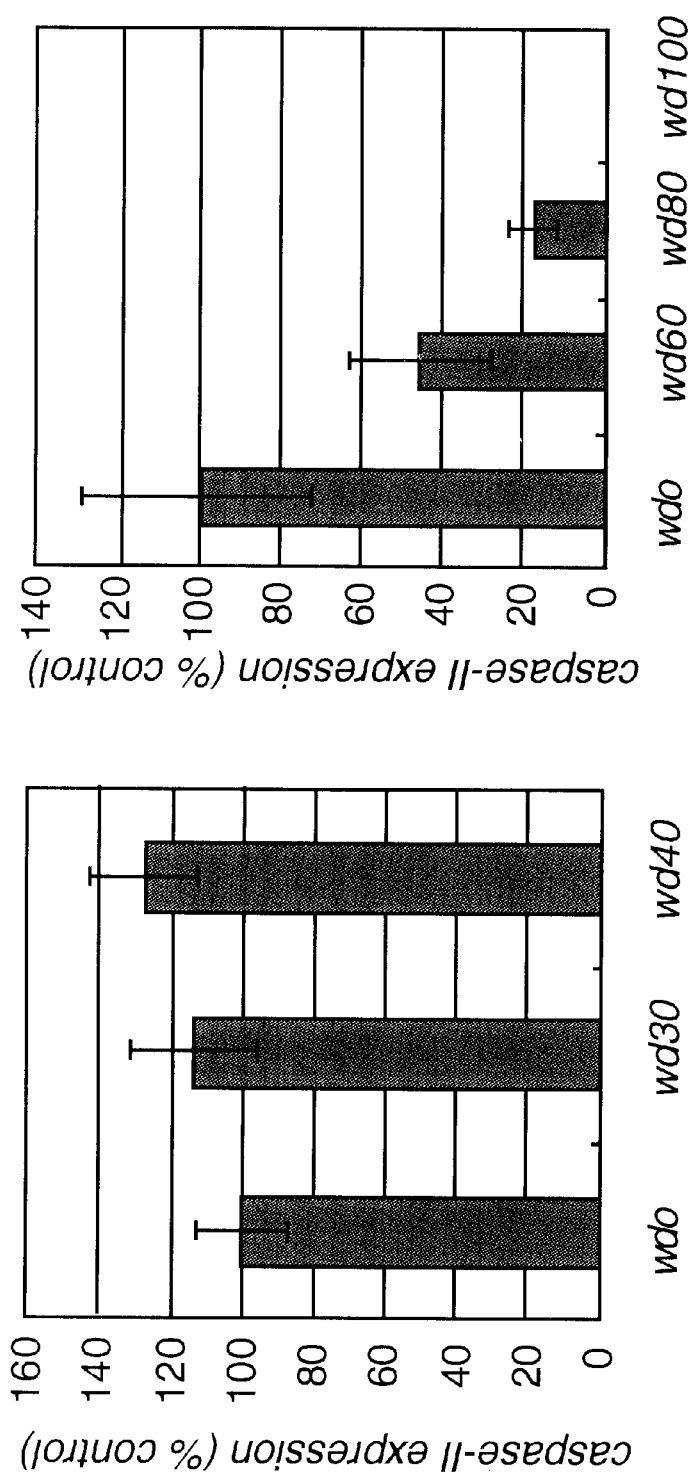
FIG. 27 is a graph of the inhibition of caspase-11 induction by synthetic wedelolactone. BalbC/3T3 cells were treated with 0, 30 µM, 40 µM, 60µM, 80 µM or 100 µM of wedelolactone for 1 hour and LPS for an additional 6 hours. The induction of caspase-11 was measured by Western blot analysis and quantification.

To determine the activity of synthetic wedelolactone in inhibiting caspase-11 induction, the BalbC/3T3 cell assay, as described above, was used (FIG. 27). Incubating BalbC/3T3 cells with synthetic wedelolactone inhibited the induction of caspase-11 by LPS, with an IC50 of about 50 μM.

Figure 28:
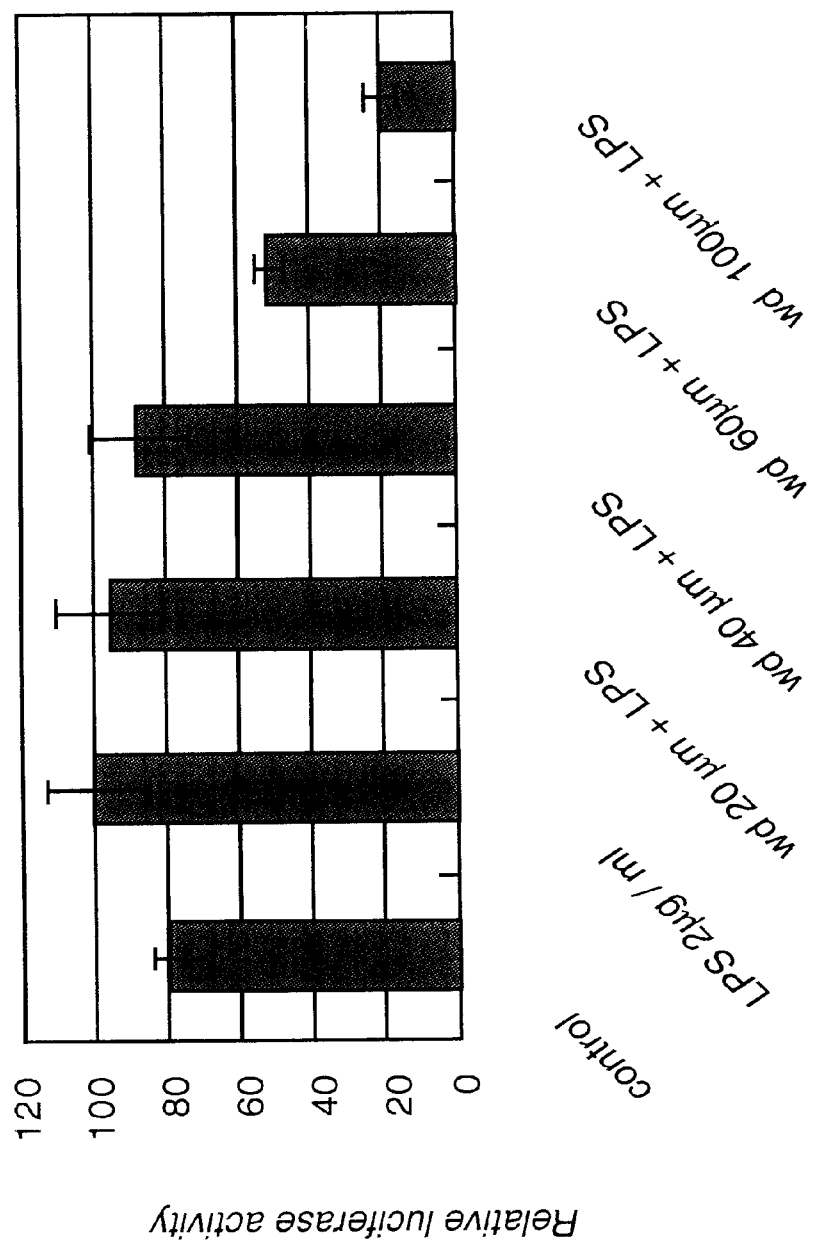
FIG. 28 is a graph of the inhibition of NF-κB activation by synthetic wedelolactone. BalbC/3T3 cells were transfected with NF-κB luciferase construct. Twelve hours later, cells were treated with 0, 20 μM, 40 μM, 60 μM, or 100 μM of wedelolactone for 1 hour and then 2 μg/ml LPS for additional 6 hours. Luciferase activity was then quantified.

The ability of synthetic wedelolactone to inhibit the activation of NF-κB induced by LPS was also assessed. BalbC/3T3 cells were transfected with a plasmid encoding an NF-κB-luciferase reporter protein in the presence of varying concentrations of wedelolactone. Similar to the result of using purified wedelolactone, synthetic wedelolactone inhibited the activation of the NF-κB promoter in the same concentration range that resulted in inhibition of caspase-11 induction (FIG. 28). These experiments provided the final confirmation that wedelolactone is an inhibitor of NF-κB activation and caspase-11 induction. Thus, wedelolactone can be used to treat cell death diseases and inflammation.

EXAMPLE 10

Wedelolactone Inhibits NF-κB and STAT1 Pathways by cDNA Array Analysis

As discussed above, wedelolactone (60 and 100 μM) inhibited the NF-κB transcriptional activity induced by LPS in BalbC/3T3 cells. mRNA expression from the BalbC/3T3 cells treated with 100 μM wedelolactone for 1 h followed by treatment with LPS for 6 h were compared with the expression in the cells that were not pretreated with wedelolactone, using an Atlas DNA array test (Clontech). One hundred μM wedelolactone reduced the expression of NF-κB p105 mRNA in LPS-treated BalbC/3T3 cells at the ratio of 1 to 8. STAT1 and STAT3 expression levels were also reduced to 4% and 30% of the expression of control cells treated with LPS only. These results indicate that wedelolactone inhibits pathways involving NF-κB, STAT1, and STAT3 transcription factors.

EXAMPLE 11

Inhibition of Caspase-11 Induction and LPS-induced Septic Shock by Wedelolactone and its Derivatives In Vivo An important test of wedelolactone activity is to see if it can pheno-copy a caspase-11 knockout mutant in inhibiting mature IL-1β secretion and lethality induced by LPS. The toxicity of wedelolactone in mice is tested by gradually increasing the dose to determine the LD50. Next, 40 μg/g body weight of LPS is co-injected with different doses of wedelolactone to see if wedelolactone can inhibit the lethality induced by LPS. Plasma is collected for measurement of IL-1β levels by an ELISA kit (R & D). Inhibition of LPS lethality and IL-1β secretion are then assessed to determine that wedelolactone can pheno-copy a caspase-11 mutant. The most effective compounds in the wedelolactone derivative library are also tested for their ability to pheno-copy the caspase-11 mutant phenotype by inhibiting IL-1β secretion and septic shock induced by LPS.

EXAMPLE 12

Identification of Protein Targets of Wedelolactone

The SAR analysis and synthesis of wedelolactone affinity reagents allows for the direct identification of protein targets of wedelolactone. For example, cytosolic and nuclear extracts of cells are applied to an affinity column of wedelolactone. The column is washed and eluted with an increasing concentration of wedelolactone. Eluted fractions are then collected and analyzed by mass spectrometry for the identification of proteins that interact with wedelolactone. The binding proteins are confirmed by further in vitro analysis using radiolabeled wedelolactone. These methods can also be used to identify protein targets of derivatives of wedelolactone.

EXAMPLE 13

High Throughput Screens for Additional Modulators of Cell Death or Inflammation

A high throughput screen for caspase-11 induction is used to identify modulators of cell death or inflammation. One such screening method involves the use of a caspase-11 promoter driven colorimetric assay. A luciferase fusion construct with the first exon of caspase-11 plus an additional 5–7 kb of upstream sequence of the caspase-11 promoter region is first constructed. The upstream sequence of the caspase-11 gene is obtained using standard genomic cloning techniques known to one skilled in the art. This construct is transfected into Balbc/3T3 cells to test the inducibility of luciferase expression by LPS using methods described above. The promoter region is defined by a series of sequential deletion constructs to reduce the 5' region included in the construct to contain a minimum sequence required for maintaining a proper induction pattern. If the 5' region is not sufficient for LPS induction, additional downstream sequences may be included in the vector until an LPS-inducible construct is obtained.

This caspase-11-luciferase construct is used to screen for additional compounds that are effective in inhibiting caspase-11 induction. For example, we have identified over 30 candidate herbs that may be screened. This caspase-11-luciferase construct is also used to screen the combinatorial chemical library described above, the ChemBridge compound libraries, as well as additional Chinese herb extracts for inhibitors of caspase-11 induction.

EXAMPLE 14

Identification of Cell Death or Inflammation Modulators by Screening for Inhibitors of the NF-κB Pathway Since caspase-11 induction is mediated through the activation of the NF-κB pathway, an alternative approach for the identification of cell death or inflammation modulators is to directly screen for inhibitors of the NF-κB pathway. This system is based on the T-Rex tetracycline inducible system (Invitrogen). To generate an NF-κB responsive system the NF-κB response element was introduced into pcDNA6/TR vector upstream from tetracycline repressor gene (TetR) (Invitrogen), replacing the constitutively active CMV promoter. This was achieved by PCR amplification of the NF-κB heterologous promoter from the NF-κB-Luciferase vector (Stratagene) and its introduction between the Sac I/Spe I sites of the pcDNA6/TR vector, which simultaneously eliminates the CMV promoter. In the new pNFkB-TR vector expression of TetR protein is controlled by NF-κB induction.

Luciferase activity was selected as an optimal output for the screen due to its high sensitivity and low background. Therefore the luciferase gene from the pGL3 vector (Promega) was introduced between the Hind III and Xba I sites of tetracycline operator-containing pTO vector (Invitrogen). Overall, in this system, induction of NF-κB activity in response to LPS results in a reduction in luciferase expression. Activation of NF-κB results in an induction of TetR expression, which binds to the tetracycline operator in the pTO-Luc vector and inhibits luciferase expression. Attenuation of NF-κB induction by a small molecule inhibitor results in an increase in luciferase expression, indicated as a positive readout, instead of a negative readout. This method allows for the distinction of selective NF-κB repressors from generally toxic compounds, which are a possibility with a system with a negative readout.

All publications and patent applications mentioned in this specification are herein incorporated by reference to the same extent as if each independent publication or patent application was specifically and individually indicated to be incorporated by reference.

While the invention has been described in connection with specific embodiments thereof, it will be understood that it is capable of further modifications and this application is intended to cover any variations, uses, or adaptations of the invention following, in general, the principles of the invention and including such departures from the present disclosure come within known or customary practice within the art to which the invention pertains and may be applied to the essential features hereinbefore set forth, and follows in the scope of the appended claims.

What is claimed is:

1. A method for treating or preventing a cell death disease in a subject, said method comprising administering wedelolactone, or a derivative or salt thereof, to said subject, wherein said cell death disease is not caused by hepatotoxicity.

2. A method for treating or preventing a septic shock in a subject, said method comprising administering wedelolactone, or a derivative or salt thereof, to said subject.

3. A method for treating or preventing septic shock in a subject, said method comprising administering to the subject a chemical compound in a pharmaceutically acceptable carrier, said compound having the formula:

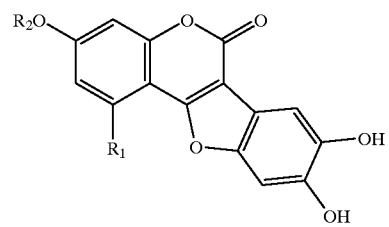

wherein $R_1$ is selected from the group consisting of H, OH, and $OCH_3$; and $R_2$ is selected from the group consisting of H, $CH_3$, and $(CH_2)_x CH_3$, wherein x is a positive integer.

4. The method of claim 1 or 2, wherein said wedelolactone is present in an extract from a plant.

5. The method of claim 4, wherein said wedelolactone is substantially pure.

6. A method for treating or preventing a cell death disease in a subject, said method comprising administering to the subject a chemical compound in a pharmaceutically acceptable carrier, said compound having the formula:

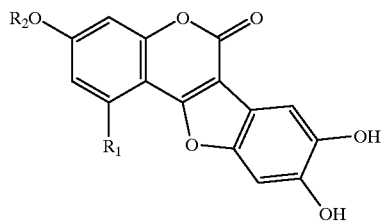

wherein $R_1$ is selected from the group consisting of H, OH, and $OCH_3$; and $R_2$ is selected from the group consisting of H, $CH_3$, and $(CH_2)_xCH_3$, wherein x is a positive integer, wherein said cell death disease is not caused by hepatotoxicity.

7. The method of claim 6 or 3, wherein in the compound $R_1$ is OH and $R_2$ is $CH_3$.

8. The method of claim 1 or 6, wherein said cell death disease is a neurodegenerative disease.

9. The method of claim 8, wherein said neurodegenerative disease is selected from the group consisting of ischemic brain injury and stroke.

10. The method of claim 1, 6, 2, or 3, wherein said subject is a mammal.

11. The method of claim 10, wherein said subject is a human.

12. The method of claim 10, wherein said subject is a rodent.

13. A method of synthesizing a 2,3-disubstituted benzo[b]furan, said method comprising subjecting a molecule having the formula:

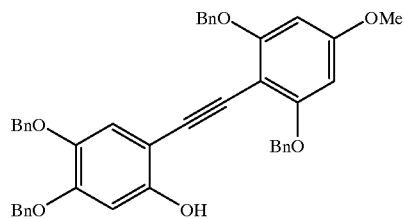

to carbonylative heteroannulation.

14. The method of claim 13, wherein said molecule is in reaction with CO and $CH_3OH$.

15. The method of claim 13, wherein said carbonylative heteroannulation occurs in the presence of $PdI_2$-thiourea, $CBr_4$, and $CsCO_3$.

16. A method of synthesizing wedelolactone, said method comprising subjecting a molecule having the formula:

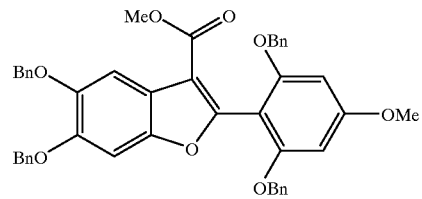

to lactonization.

* * * * *